(12) United States Patent
Bisacchi et al.

(10) Patent No.: US 7,144,895 B2
(45) Date of Patent: Dec. 5, 2006

(54) BENZENE ACETAMIDE COMPOUNDS USEFUL AS SERINE PROTEASE INHIBITORS

(75) Inventors: Gregory S. Bisacchi, Ringoes, NJ (US); George C. Morton, Collegeville, PA (US)

(73) Assignee: Bristol-Myers Squibb Co., Princeton, NJ (US)

( * ) Notice: Subject to any disclaimer, the term of this patent is extended or adjusted under 35 U.S.C. 154(b) by 169 days.

(21) Appl. No.: 10/775,443

(22) Filed: Feb. 10, 2004

(65) Prior Publication Data

US 2004/0176375 A1 Sep. 9, 2004

Related U.S. Application Data

(60) Provisional application No. 60/446,578, filed on Feb. 11, 2003.

(51) Int. Cl.
*A61K 31/472* (2006.01)
*C07D 217/22* (2006.01)

(52) U.S. Cl. ............... 514/310; 546/143; 546/146; 546/139; 514/307

(58) Field of Classification Search ........... 514/310, 514/307; 546/143, 139, 146
See application file for complete search history.

(56) References Cited

U.S. PATENT DOCUMENTS

| | | | |
|---|---|---|---|
| 6,140,353 | A | 10/2000 | Ackermann et al. |
| 6,194,409 | B1 | 2/2001 | Van Boeckel et al. |
| 6,242,644 | B1 | 6/2001 | Ackermann et al. |
| 6,335,324 | B1 | 1/2002 | Bisacchi et al. |
| 6,358,960 | B1 | 3/2002 | Senokuchi et al. |
| 6,472,393 | B1 | 10/2002 | Aliagas-Martin et al. |
| 6,642,252 | B1 | 11/2003 | Bisacchi et al. |
| 6,699,994 | B1 | 3/2004 | Babu et al. |

FOREIGN PATENT DOCUMENTS

| | | |
|---|---|---|
| WO | WO 96/20689 | 7/1996 |
| WO | WO 97/10214 | 3/1997 |
| WO | WO 01/44172 | 6/2001 |
| WO | WO 01/90051 | 11/2001 |
| WO | WO 02/09688 | 2/2002 |
| WO | WO 2002/034711 | 5/2002 |
| WO | WO2003013531 | 2/2003 |
| WO | WO 03/66588 | 8/2003 |
| WO | WO 2003/084533 | 10/2003 |
| WO | WO 2004/072101 | 8/2004 |

OTHER PUBLICATIONS

U.S. Appl. No. 10/775,923, filed Feb. 10, 2004, Glunz et al.
Stedman's Medical Dictionary, 27th Edition Illustrated in Color, Lippincott Williams & Wilkins, 1999, pp. 1711, 1831, 1832.
Dorland's Illustrated Medical Dictionary, 29th Edition, W.B. Saunders Company, 2000, pp. 1836, 1837.
Robbins Pathologic Basis of Disease, Sixth Edition, W. B. Saunders Company, 1999, pp. 113-138.
Hurst's The Heart, 10th Edition, 2001, pp. 1373-1384.
Harrison's Principles of Internal Medicine, 14th Edition, vol. 2, 1998, pp. 2325-2348.

*Primary Examiner*—Charanjit S. Aulakh
(74) *Attorney, Agent, or Firm*—Jing G. Sun; Anastasia P. Winstow

(57) ABSTRACT

Compounds having the formula (I),

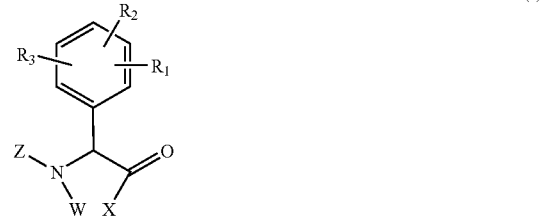

and pharmaceutically-acceptable salts, hydrates, or prodrugs thereof, are useful as serine protease inhibitors, wherein X is —OH, —O(alkyl), —O(aryl), —O(arylalkyl), —NR$_5$(aryl), or —NR$_5$(arylalkyl); W is hydrogen or —(CR$_7$R$_8$)$_q$—W$_1$; W$_1$ is hydrogen or a bond with R$_6$; Z is a 5-membered heteroaryl group, a five to six membered heterocyclo or cycloalkyl group, a 9 to 10 membered bicyclic aryl or heteroaryl, or a six membered aryl or heteroaryl, and R$_1$, R$_2$, R$_3$, R$_5$, R$_6$, R$_7$, and R$_{16}$ are as defined in the specification.

40 Claims, No Drawings

BENZENE ACETAMIDE COMPOUNDS USEFUL AS SERINE PROTEASE INHIBITORS

CROSS-REFERENCE TO RELATED APPLICATIONS

The present application claims the priority benefit of U.S. Provisional Application No. 60/446,578, filed Feb. 11, 2003, which is expressly incorporated fully herein by reference.

FIELD OF THE INVENTION

The present invention relates to benzene acetamide compounds that are inhibitors of serine proteases such as Factor VIIa. These compounds are useful as anticoagulants in treating and preventing cardiovascular diseases, as anti-inflammatory agents, and as metastasis inhibitors in treating cancer.

BACKGROUND OF THE INVENTION

Under normal conditions, the coagulation system is naturally balanced in favor of anticoagulation by a number of proteins circulating in the blood. These proteins include antithrombin III, a serine-protease inhibitor, and protein C, a vitamin-K dependent protein formed in the liver. When injury or trauma occurs, thrombin is produced at precise levels through an ordered series of reactions. Thrombin is a proteolytic enzyme that occupies a central position in the coagulation process. Thrombin catalyzes the conversion of fibrinogen to fibrin, is a key effector enzyme for blood clotting, and is pivotal for other functions as well, such as activation of helper proteins (including Factors V and VIII and thrombomodulin), and its own activation. Disturbances in the natural balance between pro- and anti-coagulant forces may result in bleeding or thrombotic diseases.

A number of coagulation factors present in the blood as precursors (e.g., Factors VII–XII) lead to the production of thrombin. When the coagulation system is triggered (e.g., when trauma occurs), the coagulation factors are transformed into activated factors (e.g., Factors VIIa, IXa, Xa, XIa, etc.) When Factor VII is activated, it forms a complex with tissue factor, a membrane protein. Thus, Factor VIIa is present as a complex bound to tissue factor. When triggered, the coagulation factors and tissue factor complexes undergo an ordered chain of reactions that ultimately lead to conversion of Factor X to Factor Xa, and Factor Xa catalyzes the conversion of prothrombin to thrombin.

An elevated plasma level of coagulation factors, particularly Factor VIIa, is a risk factor for fatal myocardial infarction and associated with coronary artery disease and other abnormalities of the coagulation system, e.g., thrombosis, ischemic vascular disease, intravascular clotting, stroke, embolisms, and so forth. Accordingly, antithrombotic agents have been researched and developed for use in treating cardiovascular and other diseases. Presently established antithrombotic agents include heparin, coumarin, and aspirin. There are, however, limitations with these agents. For example, both heparin and coumarin have a highly-variable dose-related response, and their anticoagulant effects must be closely monitored to avoid a risk of serious bleeding. The erratic anticoagulant response of heparin is likely due to its propensity to bind non-specifically to plasma proteins. Aspirin has a limited efficacy and at high doses presents a risk of gastrointestinal bleeding. Thrombin inhibitors and their drawbacks are further discussed in WO 96/20689.

As may be appreciated, those in the field of pharmaceutical research continue to seek new compounds and compositions having increased effectiveness and bioavailability and/or having fewer side effects. There is particularly an interest in developing agents that can selectively and directly inhibit key factors in the complicated coagulation process. Compounds effective in inhibiting Factors VIIa, Xa, as well as tryptase and urokinase are described in U.S. Pat. Nos. 6,335,324 and 6,642,252. Factor VIIa inhibitors are also disclosed in U.S. Pat. No. 6,358,960 and WO 01/44172. U.S. Pat. No. 6,194,409 discloses certain bicyclic groups such as isoquinoline groups which reportedly are advantageous for promoting pharmacological properties. Phenyl glycine derivatives useful as serine protease inhibitors are disclosed in U.S. Pat. Nos. 6,140,353, 6,242,644, WO 01/90051 and WO 03/66588 and U.S. Pat. No. 6,472,393.

The patents, patent applications, and articles cited above are incorporated herein by reference.

SUMMARY OF THE INVENTION

Accordingly, the present invention provides novel compounds according to formula (I):

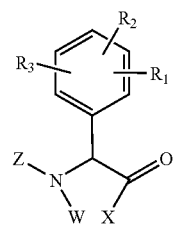

(I)

which are useful as selective inhibitors of serine protease enzymes, especially factor VIIa, or a stereoisomer or a pharmaceutically-acceptable salt, hydrate, or prodrug thereof, wherein:

X is —OH, —O(alkyl), —O(aryl), —O(arylalkyl), —NR$_5$(aryl), or —NR$_5$(arylalkyl); wherein said aryl or arylalkyl are optionally substituted with one to two R$_{25}$;

W is hydrogen or —(CR$_7$R$_8$)$_q$—H;

Z is a 5-membered heteroaryl group optionally substituted with 1–3 R$_9$, a five to six membered heterocyclo or cycloalkyl group optionally substituted with 1–3 R$_9$, a 9 to 10 membered bicyclic aryl or heteroaryl optionally substituted with 1–3 substituents selected from R$_9$ and/or R$_{10}$, or

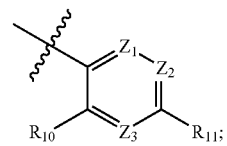

Z$_1$, Z$_2$ and Z$_3$ are independently N or CR$_9$;

R$_1$, R$_2$ and R$_3$ are attached to any available carbon atom of phenyl ring A and are independently selected from hydrogen, halogen, cyano, nitro, C$_{1-10}$alkyl, C$_{2-10}$alkenyl, substituted C$_{1-10}$alkyl, substituted C$_{2-10}$alkenyl, —C(=O)NR$_{12}$R$_{13}$, —OR$_{12}$, —CO$_2$R$_{12}$, —C(=O)R$_{12}$, —SR$_{12}$, —S(O)$_r$R$_{15}$, —NR$_{12}$R$_{13}$, —NR$_{12}$SO$_2$R$_{15}$, —NR$_{14}$SO$_2$NR$_{12}$R$_{13}$, —NR$_{12}$CO$_2$R$_{13}$, —NR$_{12}$C(=O)R$_{13}$, —NR$_{14}$C(=O)NR$_{12}$R$_{13}$, —SO$_2$NR$_{12}$R$_{13}$, aryl, heteroaryl, cycloalkyl, and heterocyclo;

$R_5$ is hydrogen, $C_{1-4}$alkyl, $NH_2$, $C_{1-4}$alkylamino, hydroxy, or $C_{1-4}$alkoxy;

$R_7$ and $R_8$ are independently selected from hydrogen, —$OR_{18}$, —$NR_{18}R_{19}$, —$NR_{18}SO_2R_{20}$, alkyl, alkenyl, substituted alkyl, substituted alkenyl, halogen, haloalkyl, haloalkoxy, cyano, nitro, alkylthio, —C(=O)H, acyl, —$CO_2H$, alkoxycarbonyl, sulfonamido, sulfonyl, and phenyl in turn optionally substituted with 1–3 of halogen, cyano, haloalkyl, haloalkoxy, nitro, hydroxy, $C_{1-4}$alkyl, $C_{1-4}$hydroxyalkyl, $C_{1-4}$alkoxy, amino, $NH(C_{1-4}$alkyl), $N(C_{1-4}$ alkyl$)_2$, and/or $C_{1-4}$aminoalkyl;

$R_9$, $R_{10}$ and $R_{11}$ are independently selected from hydrogen, halogen, alkyl, substituted alkyl, haloalkyl, haloalkoxy, cyano, nitro, —$S(O)_uR_{21}$, —$NR_{22}SO_2R_{21}$, —$C(=O)NR_{22}R_{23}$, —$OR_{22}$, —$CO_2R_{22}$, —$C(=O)R_{22}$, —$SR_{22}$, —$NR_{22}R_{23}$, —$NR_{22}CO_2R_{23}$, —$NR_{22}C(=O)R_{23}$, —$NR_{22}C(=O)NR_{23}R_{24}$, —$SO_2NR_{22}R_{23}$, —$NR_{22}SO_2NR_{23}R_{24}$, —$C(=NR_{22})NR_{23}R_{24}$, five or six membered heterocyclo or heteroaryl, phenyl, and $C_{3-7}$cycloalkyl, provided that $R_{11}$ is not —$C(=NR_{22})NR_{23}R_{24}$ when W is hydrogen; wherein when $R_9$, $R_{10}$ or $R_{11}$ is selected from heterocyclo, heteroaryl, phenyl, and $C_{3-7}$cycloalkyl, each of said cyclic groups in turn is optionally substituted with up to three of $C_{1-4}$alkyl, $C_{1-4}$alkoxy, $C_{1-4}$ hydroxyalkyl, $C_{1-4}$ aminoalkyl, halogen, hydroxy, haloalkyl, haloalkoxy, amino, $C_{1-4}$ alkylamino, and/or cyano;

$R_{12}$, $R_{13}$, $R_{14}$, $R_{18}$, $R_{19}$, $R_{22}$ $R_{23}$, and $R_{24}$ are independently selected from hydrogen, alkyl, substituted alkyl, alkenyl, substituted alkenyl, aryl, heteroaryl, cycloalkyl, and heterocyclo;

$R_{15}$, $R_{20}$ and $R_{21}$ are independently selected from alkyl, substituted alkyl, alkenyl, substituted alkenyl, aryl, heteroaryl, cycloalkyl, and heterocyclo;

$R_{25}$ at each occurrence is selected from hydrogen, halogen, cyano, nitro, $C_{1-10}$alkyl, $C_{2-10}$alkenyl, substituted $C_{1-10}$alkyl, substituted $C_{2-10}$alkenyl, —$C(=O)NR_{12}R_{13}$, —$OR_{12}$, —$CO_2R_{12}$, —$C(=O)R_{12}$, —$SR_{12}$, —$S(O)_tR_{15}$—$NR_{12}R_{13}$, —$NR_{12}SO_2R_{15}$, —$NR_{14}SO_2NR_{12}R_{13}$, —$NR_{12}CO_2R_{13}$, —$NR_{12}C(=O)R_{13}$, —$NR_{14}C(=O)NR_{12}R_{13}$, —$SO_2NR_{12}R_{13}$, aryl, heteroaryl, cycloalkyl, and heterocyclo;

p is 1 or 2;

q is 1, 2 or 3;

t is 1 or 2; and u is 1 or 2;

provided that when Z is phenyl, pyridyl or pyridazinyl, $R_9$, $R_{10}$ and/or $R_{11}$ are other than cyano or —$C(=NR_{22})NR_{23}R_{24}$.

The invention also relates to pharmaceutical compositions containing at least one compound of formula (I) and a pharmaceutically-acceptable carrier or diluent, for use in treating serine protease or Factor VIIa-associated diseases. Also included within the invention are methods of treating such diseases comprising administering to a mammal in need of such treatment an effective amount of at least one compound of formula (I). Further included in the invention are compositions for use as anticoagulants during the preparation, use, storage, or fractionation of blood and methods of maintaining blood in the fluid phase during its preparation, use, storage or fractionation.

DETAILED DESCRIPTION OF THE INVENTION

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention. All tautomers of shown or described compounds are also considered to be part of the present invention.

The following are definitions of terms used in this specification. The initial definition provided for a group or term herein applies to that group or term throughout the present specification, individually or as part of another group, unless otherwise indicated.

Preferably, the molecular weight of compounds of the present invention is less than about 500, 550, 600, 650, 700, 750, or 800 grams per mole. Preferably, the molecular weight is less than about 800 grams per mole. More preferably, the molecular weight is less than about 750 grams per mole. Even more preferably, the molecular weight is less than about 700 grams per mole.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. Ring double bonds, as used herein, are double bonds that are formed between two adjacent ring atoms (e.g., C=C, C=N, or N=N). The present invention, in general, does not cover groups such as N-halo, S(O)H, and $SO_2H$.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

The term "alkyl" refers to straight or branched chain hydrocarbon groups having 1 to 12 carbon atoms, preferably 1 to 8 carbon atoms. Lower alkyl groups, that is, alkyl groups of 1 to 4 carbon atoms, are most preferred. When numbers appear in a subscript after the symbol "C", the subscript defines with more specificity the number of carbon atoms that a particular group may contain. For example, "$C_{1-6}$alkyl" refers to straight and branched chain alkyl groups with one to six carbon atoms, such as methyl, ethyl, n-propyl, isopropyl, n-butyl, t-butyl, n-pentyl, and so forth. When the subscript "0" is used, as in $C_0$, this refers to a bond. Thus, the term $C_{0-2}$hydroxyalkyl refers to hydroxy, hydroxymethyl, and hydroxyethyl.

The term "substituted alkyl" refers to an alkyl group as defined above having one, two, or three substituents selected from the group consisting of halogen, trifluoromethyl, alkenyl, alkynyl, nitro, cyano, keto (=O), haloalkoxy, —OR, —SR, —NRR', —NRSO$_2$, —NRSO$_2$R', —SO$_2$R", —SO$_2$NRR', —CO$_2$R, —C(=O)R, —C(=O)NRR', —OC(=O)R, —OC(=O)NRR', —NRC(=O)R', —NRCO$_2$R', =N—OH, =N—O-alkyl, aryl, heteroaryl, heterocyclo and cycloalkyl, wherein R and R' are selected from hydrogen, alkyl, alkenyl, amino, alkylamino, substituted alkylamino, benzyl, phenylethyl, cycloalkyl, heterocyclo, aryl, and heteroaryl, or R and R' together may form a heterocyclo or heteroaryl ring, and R" is alkyl, alkenyl, benzyl, phenylethyl, cycloalkyl, heterocyclo, aryl, and/or heteroaryl. When an alkyl is substituted with an aryl, heteroaryl, heterocyclo or cycloalkyl, those groups are as recited below and thus optionally may be substituted as recited below. Each of R, R', and R" in turn may have zero to three substituents (preferably 0–2 substituents), appropriately selected from R''', C$_{1-4}$ alkyl, and C$_{1-4}$alkyl substituted with R''', wherein R''' is selected from halogen, haloalkyl, C$_{2-5}$alkenyl, nitro, cyano, —OH, —O(C$_{1-4}$alkyl), haloalkoxy, phenyl, benzyl, phenylethyl, phenyloxy, benzyloxy, —SH, —S(C$_{1-4}$alkyl), —S(phenyl), —NH$_2$, —NH(C$_{1-4}$alkyl), —N(C$_{1-4}$alkyl)$_2$, —NH(cycloalkyl), —NHSO$_2$, —NHSO$_2$(C$_{1-4}$alkyl), —SO$_2$(C$_{1-4}$alkyl), —SO$_2$NH$_2$, —SO$_2$NH(C$_{1-4}$alkyl), —SO$_2$N(C$_{1-4}$ alkyl)$_2$, —CO$_2$H, —CO$_2$(C$_{1-4}$alkyl), —C(=O)H, —C(=O)C$_{1-4}$alkyl, —C(=O)NH$_2$, —C(=O)NH(C$_{1-4}$alkyl), —C(=O)N(C$_{1-4}$alkyl)$_2$, —OC(=O)C$_{1-4}$alkyl, —OC(=O)NH$_2$, —OC(=O)NH(C$_{1-4}$alkyl), —OC(=O)N(C$_{1-4}$alkyl)$_2$, —NHC(=O)C$_{1-4}$alkyl, —NHCO$_2$(C$_{1-4}$alkyl), C$_{3-7}$cycloalkyl, C$_{5-6}$heteroaryl, and C$_{4-7}$heterocyclo.

When the term alkyl is used as a suffix with a second named group, as in arylalkyl or cycloalkylalkyl, this refers to a substituted alkyl in which at least one of the substituents is the second named group. For example, the term arylalkyl includes benzyl and any other straight or branched chain alkyl having at least one aryl group attached at any point of the alkyl chain. Other substituents may be attached to the alkyl chain or the second named group. Such substituents may be selected as appropriate from the groups recited above in the definition of substituted alkyl and/or from those recited herein for the second named group.

The term "alkenyl" refers to straight or branched chain hydrocarbon groups having 2 to 12 carbon atoms and at least one double bond. Alkenyl groups of 2 to 6 carbon atoms and having one double bond are most preferred.

The term "alkynyl" refers to straight or branched chain hydrocarbon groups having 2 to 12 carbon atoms and at least one triple bond. Alkynyl groups of 2 to 6 carbon atoms and having one triple bond are most preferred.

The term "alkylene" refers to bivalent straight or branched chain hydrocarbon groups having 1 to 12 carbon atoms, preferably 1 to 8 carbon atoms, e.g., {—CH$_2$—}$_n$, wherein n is 1 to 12, preferably 1–8. Lower alkylene groups, that is, alkylene groups of 1 to 4 carbon atoms, are most preferred. The terms "alkenylene" and "alkynylene" refer to bivalent radicals of alkenyl and alknyl groups, respectively, as defined above.

When reference is made to a substituted alkylene, alkenylene, or alkynylene, these groups are substituted with one to three substitutents as defined above for alkyl groups. A substituted alkylene, alkenylene, or alkynylene may have a ringed substituent attached in a spiro fashion as in

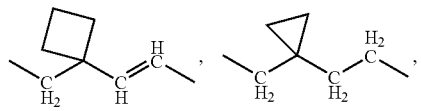

and so forth.

The term "alkoxy" refers to the group —OR, wherein R is alkyl or alkenyl. The term "alkylthio" refers to the group —SR, wherein R is alkyl or alkenyl. The term "alkylamino" refers to the group —NR'R", wherein each of R' and R" is selected from hydrogen, alkyl, alkenyl, cycloalkyl, aryl, heteroaryl, or heterocyclo, as defined herein, provided that both R' and R" are not hydrogen. The term "amino" refers to —NH$_2$. A substituted alkoxy, alkylthio, or alkylamino may have zero to three substituents as defined above for substituted alkyl.

When a subscript is used with an alkoxy, alkylthio or alkylamino, the subscript refers to the number of carbon atoms that the group may contain in addition to heteroatoms. Thus, for example, monovalent C$_{1-2}$alkylamino includes the groups —NHCH$_3$, —NHCH$_2$CH$_3$, and —N(CH$_3$)$_2$. A lower alkylamino comprises an alkylamino having one to four carbon atoms.

The alkoxy, alkylthio, or alkylamino groups may be monovalent or bivalent. By "monovalent" it is meant that the group has a valency (i.e., power to combine with another group), of one, and by "bivalent" it is meant that the group has a valency of two. For example, a monovalent alkoxy includes groups such as —O—C$_{1-12}$alkyl, whereas a bivalent alkoxy includes groups such as —O—C$_{1-12}$alkylene-, etc.

The term "acyl" refers to a carbonyl {—C(=O)—} linked to an organic group i.e.,

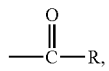

wherein R may be selected from alkyl, substituted alkyl, alkenyl, substituted alkenyl, aryl, heterocyclo, cycloalkyl, and heteroaryl, as defined herein.

The term "alkoxycarbonyl" refers to a carboxy or ester group {—CO$_2$—} linked to an organic radical, i.e.,

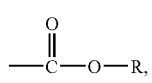

wherein R is as defined for acyl. "Carboxy" refers to the group CO$_2$H, and "carboxyalkyl" refers to —R—CO$_2$H, wherein R is alkylene or substituted alkylene.

The term "carbamyl" refers to a functional group in which a nitrogen atom is directly bonded to a carbonyl, i.e., as in —NRC(=O)R' or —C(=O)NRR', wherein R and R' can be hydrogen, alkyl, substituted alkyl, alkenyl, substituted alkenyl, alkoxy, cycloalkyl, aryl, heterocyclo, or heteroaryl.

The term "heteroatoms" shall include oxygen, sulfur and nitrogen.

"Halo" or "halogen" as used herein refers to fluoro, chloro, bromo, and iodo; and "counterion" is used to represent a small, negatively charged species such as chloride, bromide, hydroxide, acetate, and sulfate.

The term "haloalkyl" means an alkyl having one or more halo substituents and thus includes, for example, trifluoromethyl.

The term "perfluoroalkyl" means an alkyl group having from one to five fluoro atoms, such as pentafluoroethyl. The term "perfluoromethyl" means a methyl group substituted by one, two, or three fluoro atoms, i.e., —$CH_2F$, —$CHF_2$ and $CF_3$.

The term "haloalkoxy" means an alkoxy group having one or more halo substituents. For example, "haloalkoxy" includes —$OCF_3$.

The term "sulfonyl" refers to a sulphoxide group (i.e., —$S(O)_{1-3}$) linked to an organic radical R", wherein R" is alkyl, substituted alkyl, alkenyl, substituted alkenyl, cycloalkyl, heterocyclo, heteroaryl, or aryl. Sulfonic acid is —$SO_3H$.

The term "sulfonamide" or "sulfonamido" refers to the group —$S(O)_2NRR'$, wherein R and R' are selected from hydrogen, alkyl, substituted alkyl, alkenyl, substituted alkenyl, cycloalkyl, heterocyclo, heteroaryl and aryl. Preferably when one of R and R' is optionally substituted cycloalkyl, heterocyclo, heteroaryl or aryl (as defined below), the other of R and R' is hydrogen or alkyl.

The term "cycloalkyl" refers to fully saturated and partially unsaturated substituted or unsubstituted hydrocarbon rings of 3 to 9, preferably 3 to 7 carbon atoms. When substituted, the cycloalkyl will contain one to three (preferably one to two) groups selected from the group consisting of $C_{0-6}$alkyl optionally substituted with (or linked to) one to two of halogen, perfluoroalkyl, alkenyl, alkynyl, nitro, cyano, keto (=O), haloalkoxy, —OR, —SR, —NRR', —$NRSO_2$, —$NRSO_2R'$, —$SO_2R"$, —$SO_2NRR'$, —$CO_2R$, —C(=O)R, —C(=O)NRR', —OC(=O)R, —OC(=O)NRR', —NRC(=O)R', —$NRCO_2R'$, =N—OH, =N—O-alkyl, phenyl, 3 to 6 membered heteroaryl or heterocyclo, and/or $C_{3-7}$cycloalkyl, wherein R and R' are independently selected from hydrogen, alkyl, alkenyl, phenyl, benzyl, phenylethyl, $C_{3-7}$cycloalkyl, and 3 to 6 membered heterocyclo or heteroaryl, and R" is alkyl, alkenyl, phenyl, benzyl, phenylethyl, $C_{3-7}$cycloalkyl, and/or 3 to 6 membered heterocyclo or heteroaryl. The term "cycloalkyl" also includes such rings having a phenyl ring fused thereto or having a carbon-carbon bridge of 3 to 4 carbon atoms. Additionally, each of R, R' and R" in turn may, as appropriate, be optionally substituted with one to two $C_{0-4}$alkyl optionally substituted with (or linked to) one to two of halogen, $CF_3$, $OCF_3$, alkenyl, nitro, cyano, keto (=O), hydroxy, alkoxy, SH, S(alkyl), $NH_2$, NH(alkyl), N(alkyl)$_2$, $CO_2H$, $CO_2$(alkyl), C(=O)H, and/or C(=O)alkyl.

The term "aryl" refers to phenyl and naphthyl, with phenyl being preferred. The term "aryl" includes such rings having zero to three substituents (preferably 0–2 substituents). When substituted, the aryl will contain one to three $C_{0-6}$alkyl optionally substituted with (or linked to) one to two of halogen, perfluoroalkyl, alkenyl, alkynyl, nitro, cyano, haloalkoxy, —OR, —SR, —NRR', —$NRSO_2$, —$NRSO_2R'$, —$SO_2R"$, —$SO_2NRR'$, —$CO_2R$, —C(=O)R, —C(=O)NRR', —OC(=O)R, —OC(=O)NRR', —NRC(=O)R', —$NRCO_2R'$, phenyl, 3 to 6 membered heteroaryl or heterocyclo, and $C_{3-7}$cycloalkyl, wherein R and R' are independently selected from hydrogen, alkyl, alkenyl, phenyl, benzyl, phenylethyl, $C_{3-7}$cycloalkyl, or 3 to 6 membered heterocyclo or heteroaryl, and R" is alkyl, alkenyl, phenyl, benzyl, phenylethyl, $C_{3-7}$cycloalkyl, and/or 3 to 6 membered heterocyclo or heteroaryl. Additionally, two substituents attached to an aryl, particularly a phenyl group, may join to form a further ring including a spiro ring or a fused ring, e.g., spiro-cyclopentyl or fused cyclohexenyl, or fused heteroaryl or heterocyclo. Each of R, R', and R" in turn may, as appropriate, be optionally substituted with one to two $C_{0-4}$alkyl optionally substituted with (or linked to) one to two of halogen, $CF_3$, $OCF_3$, alkenyl, nitro, cyano, keto (=O), hydroxy, alkoxy, SH, S(alkyl), $NH_2$, NH(alkyl), N(alkyl)$_2$, $CO_2H$, $CO_2$(alkyl), C(=O)H, and/or C(=O) alkyl.

The term "heterocyclo" refers to substituted and unsubstituted non-aromatic 3 to 7 membered monocyclic groups, 7 to 11 membered bicyclic groups, and 10 to 15 membered tricyclic groups, in which at least one of the rings has at least one heteroatom (O, S or N). Each ring of the heterocyclo group containing a heteroatom can contain one or two oxygen or sulfur atoms and/or from one to four nitrogen atoms, provided that the total number of heteroatoms in each ring is four or less, and further provided that the ring contains at least one carbon atom and no two adjacent heteroatoms are simultaneously selected from —O— and —S—. The fused rings completing bicyclic and tricyclic groups may contain only carbon atoms and may be saturated, partially saturated, or unsaturated. The nitrogen and sulfur atoms may optionally be oxidized and the nitrogen atoms may optionally be quaternized. The heterocyclo group may be attached at any available nitrogen or carbon atom. The heterocyclo ring may contain zero to three substituents (preferably 0–2 substituents), selected from $C_{0-6}$alkyl optionally substituted with (or linked to) one to two of halogen, perfluoroalkyl, alkenyl, alkynyl, nitro, cyano, haloalkoxy, keto (=O), —OR, —SR, —NRR', —$NRSO_2$, —$NRSO_2R'$, —$SO_2R"$, —$SO_2NRR'$, —$CO_2R$, —C(=O)R, —C(=O)NRR', —OC(=O)R, —OC(=O)NRR', —NRC(=O)R', —$NRCO_2R'$, phenyl, 3 to 6 membered heteroaryl or heterocyclo, and/or $C_{3-7}$cycloalkyl, wherein R and R' are independently selected from hydrogen, alkyl, alkenyl, phenyl, benzyl, phenylethyl, $C_{3-7}$cycloalkyl, and 3 to 6 membered heterocyclo or heteroaryl, and R" is alkyl, alkenyl, phenyl, benzyl, phenylethyl, $C_{3-7}$cycloalkyl, or 3 to 6 membered heterocyclo or heteroaryl. The term "heterocyclo" also includes such rings having a phenyl ring fused thereto or having a carbon-carbon bridge of 3 to 4 carbon atoms. Additionally, each of R, R' and R" in turn may, as appropriate, be optionally substituted with one to two $C_{0-4}$alkyl optionally substituted with (or linked to) one to two of halogen, $CF_3$, $OCF_3$, alkenyl, nitro, cyano, keto (=O), hydroxy, alkoxy, SH, S(alkyl), $NH_2$, NH(alkyl), N(alkyl)$_2$, $CO_2H$, $CO_2$(alkyl), C(=O)H, and/or C(=O)alkyl. Exemplary monocyclic groups include oxiranyl, aziridinyl, pyrrolidinyl, imidazolinyl, imidazolidinyl, pyrazolidinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, tetrahydropyranyl, morpholinyl, thiamorpholinyl, and the like. Exemplary bicyclic heterocyclo groups include quinuclidinyl.

The term "heteroaryl" refers to substituted and unsubstituted aromatic 5 to 7 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms, provided that the total number of heteroatoms in each ring is four or less, each ring has at least one carbon atom, and no two adjacent heteroatoms are simultaneously selected from —O— and —S—. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring, but the other fused ring or rings may be aromatic or non-aromatic. The heteroaryl group may be attached at any available nitrogen or carbon atom of any ring. The heteroaryl ring system may contain zero to three substituents (preferably 0–2 substituents), selected from $C_{0-6}$alkyl optionally substituted with (or linked to) one to two of halogen, perfluoroalkyl, alkenyl, alkynyl, nitro, cyano, haloalkoxy, keto (=O), —OR, —SR, —NRR', —NRSO$_2$, —NRSO$_2$R', —SO$_2$R", —SO$_2$NRR', —CO$_2$R, —C(=O)R, —C(=O)NRR', —OC(=O)R, —OC(=O)NRR', —NRC(=O)R', —NRCO$_2$R', phenyl, 3 to 6 membered heteroaryl or heterocyclo, and/or $C_{3-7}$cycloalkyl, wherein R and R' are independently selected from hydrogen, alkyl, alkenyl, phenyl, benzyl, phenylethyl, $C_{3-7}$cycloalkyl, and 3 to 6 membered heterocyclo or heteroaryl, and R" is alkyl, alkenyl, phenyl, benzyl, phenylethyl, $C_{3-7}$cycloalkyl, and/or 3 to 6 membered heterocyclo or heteroaryl. Additionally, each of R, R' and R" in turn may, as appropriate, be optionally substituted with one to two $C_{0-4}$alkyl optionally substituted with (or linked to) one to two of halogen, $CF_3$, $OCF_3$, alkenyl, nitro, cyano, keto (=O), OH, O(alkyl), phenyloxy, benzyloxy, SH, S(alkyl), $NH_2$, NH(alkyl), N(alkyl)$_2$, $CO_2H$, $CO_2$(alkyl), C(=O)H, and/or C(=O)alkyl.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, indazolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, cinnolinyl, quinoxalinyl, indazolyl, pyrrolopyridyl, furopyridinyl, dihydroisoindolyl, benzothiadiazolyl, phthalazinyl, benzotriazinyl, quinazolinyl, quinolinyl, benzoxazolyl, benzothiopheneyl, tetrahydrophthalazinyl, tetrahydroquinolinyl, tetrahydroquinazolinyl, tetrahydrocinnolinyl, tetrahydroquinoxalinyl and the like.

Exemplary tricyclic heteroaryl groups include carbazolyl, benzidolyl, phenanthrollinyl, acridinyl, phenanthridinyl, xanthenyl and the like.

The term "carbocyclic" means a saturated or unsaturated monocyclic or bicyclic ring in which all atoms of all rings are carbon. Thus, the term includes cycloalkyl and aryl rings. The carbocyclic ring may be substituted in which case the substituents are selected from those recited above for cycloalkyl and aryl groups, as appropriate.

When the term "unsaturated" is used herein to refer to a ring or group, the ring or group may be fully unsaturated or partially unsaturated.

Throughout the specification, groups and substituents thereof may be chosen by one skilled in the field to provide stable moieties and compounds. The terms "appropriately selected" are "appropriately substituted" as used herein are intended to mean that one skilled in the field would make selections from the recited groups to provide stable moieties and compounds.

The compounds of of the present inventions form salts which are also within the scope of this invention. Reference to a compound of the formula I herein is understood to include reference to salts thereof, unless otherwise indicated. The term "salt(s)", as employed herein, denotes acidic and/or basic salts formed with inorganic and/or organic acids and bases. In addition, when a compound of formula I contains both a basic moiety, such as, but not limited to an amine or a pyridine ring, and an acidic moiety, such as, but not limited to, a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the formula I may be formed, for example, by reacting a compound of the formula I with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines [formed with N,N-bis(dehydro-abietyl)ethylenediamine], N-methyl-D-glucamines, N-methyl-D-glucamides, t-butyl amines, and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Compounds of the present invention, and salts thereof, may exist in their tautomeric form, in which hydrogen atoms are transposed to other parts of the molecules and the chemical bonds between the atoms of the molecules are consequently rearranged. It should be understood that all tautomeric forms, insofar as they may exist, are included within the invention. Additionally, inventive compounds may have trans and cis isomers and may contain one or more chiral centers, therefore existing in enantiomeric and diastereomeric forms. The invention includes all such isomers, as well as mixtures of cis and trans isomers, mixtures of diastereomers and racemic mixtures of enantiomers (optical isomers). When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. When enantiomeric or diastereomeric products are prepared, they can be separated by conventional methods, for example, by chromatographic or fractional crystallization. The inventive compounds may be in the free or hydrate form.

Compounds of the present invention are, subsequent to their preparation, preferably isolated and purified to obtain a composition containing an amount by weight equal to or greater than 99% compound of the present invention ("substantially pure"), which is then used or formulated as described herein. Such "substantially pure" compounds are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. It is preferred that there presently recited compounds do not contain a N-halo, $S(O)_2H$, or $S(O)H$ group.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) *Design of Prodrugs*, edited by H. Bundgaard, (Elsevier, 1985), and *Methods in Enzymology*, Vol. 42, at pp. 309–396, edited by K. Widder, et. al. (Academic Press, 1985);

b) *A Textbook of Drug Design and Development*, edited by Krosgaard-Larsen and H. Bundgaard, Chapter 5, "Design and Application of Prodrugs," by H. Bundgaard, at pp. 113–191 (1991);

c) H. Bundgaard, *Advanced Drug Delivery Reviews*, Vol. 8, p. 1–38 (1992);

d) H. Bundgaard, et al., *Journal of Pharmaceutical Sciences*, Vol. 77, p. 285 (1988); and e) N. Kakeya, et. al., *Chem Phar Bull.*, Vol. 32, p. 692 (1984).

Compounds containing a carboxy group can form physiologically hydrolyzable esters which serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkylbenzyl, 4-methoxybenzyl, indanyl, phthalyl, methoxymethyl, $C_{1-6}$ alkanoyloxy-$C_{1-6}$alkyl, e.g. acetoxymethyl, pivaloyloxymethyl or propionyloxymethyl, $C_{1-6}$alkoxycarbonyloxy-$C_{1-6}$alkyl, e.g. methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

It should further be understood that solvates (e.g., hydrates) of the compounds of the present invention are also with the scope of the present invention. Methods of solvation are generally known in the art.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the present invention that is effective when administered alone or in combination to inhibit factor VIIa. "Therapeutically effective amount" is also intended to include an amount of the combination of compounds claimed that is effective to inhibit factor VIIa. The combination of compounds is preferably a synergistic combination. Synergy, as described, for example, by Chou and Talalay, *Adv. Enzyme Regul.* 1984, 22:27–55, occurs when the effect (in this case, inhibition of factor VIIa) of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased antithrombotic effect, or some other beneficial effect of the combination compared with the individual components.

Preferred Embodiments

In a preferred embodiment, the present invention provides compounds of formula (Ia):

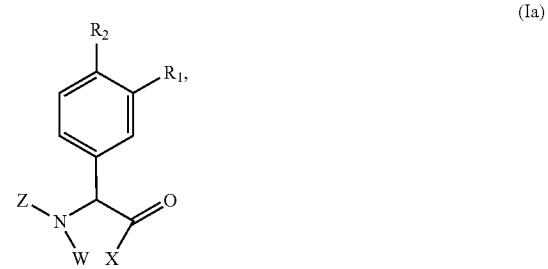

(Ia)

or a stereoisomer or a pharmaceutically-acceptable salt, hydrate or prodrug thereof, wherein:

X is —OH, —O(phenyl) optionally substituted with one to two $R_{25}$, —O(benzyl) optionally substituted with one to two $R_{25}$, —NH(phenyl) optionally substituted with one to two $R_{25}$, or —NH(benzyl) optionally substituted with one to two $R_{25}$;

W is hydrogen or —$(CH_2)_q$—H;

Z is selected from a 5-membered heteroaryl group optionally substituted with 1–3 $R_9$, a five to six membered heterocyclo or cycloalkyl group optionally substituted with 1–3 $R_9$, a 9 to 10 membered bicyclic aryl or heteroaryl optionally substituted with 1–3 substituents selected from $R_9$ and/or $R_{10}$, and

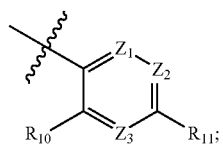

$Z_1$, $Z_2$ and $Z_3$ are independently N or $CR_9$ and at least one of $Z_1$, $Z_2$ and $Z_3$ is N;

$R_1$ and $R_2$ are independently selected from hydrogen, halogen, cyano, nitro, $C_{1-10}$alkyl, $C_{2-10}$alkenyl, substituted $C_{1-10}$alkyl, substituted $C_{2-10}$alkenyl, —C(=O)NR$_{12}$R$_{13}$, —OR$_{12}$, —CO$_2$R$_{12}$, —C(=O)R$_{12}$, —SR$_{12}$, —S(O)$_r$R$_{15}$, —NR$_{12}$R$_{13}$, —NR$_{12}$SO$_2$R$_{15}$, —NR$_{14}$SO$_2$NR$_{12}$R$_{13}$, —NR$_{12}$CO$_2$R$_{13}$, —NR$_{12}$C(=O)R$_{13}$, —NR$_{14}$C(=O)NR$_{12}$R$_{13}$, —SO$_2$NR$_{12}$R$_{13}$, aryl, heteroaryl, cycloalkyl, and heterocyclo;

$R_9$, $R_{10}$ and $R_{11}$ are independently selected from hydrogen, halogen, alkyl, substituted alkyl, haloalkyl, haloalkoxy, cyano, nitro, —S(O)$_u$R$_{21}$, —NR$_{22}$SO$_2$R$_{21}$, —C(=O)NR$_{22}$R$_{23}$, —OR$_{22}$, —CO$_2$R$_{22}$, —C(=O)R$_{22}$, —SR$_{22}$, —NR$_{22}$R$_{23}$, —NR$_{22}$CO$_2$R$_{23}$, —NR$_{22}$C(=O)R$_{23}$, —NR$_{22}$C(=O)NR$_{23}$R$_{24}$, —SO$_2$NR$_{22}$R$_{23}$, —NR$_{22}$SO$_2$NR$_{23}$R$_{24}$, —C(=NR$_{22}$)NR$_{23}$R$_{24}$, five or six membered heterocyclo or heteroaryl, phenyl, and $C_{3-7}$cycloalkyl, provided that $R_{11}$ is not —C(=NR$_{22}$)NR$_{23}$R$_{24}$ when W is hydrogen; wherein when $R_9$, $R_{10}$ or $R_{11}$ is selected from heterocyclo, heteroaryl, phenyl, and $C_{3-7}$cycloalkyl, each of said cyclic groups in turn is optionally substituted with up to three of $C_{1-4}$alkyl, $C_{1-4}$alkoxy, $C_{1-4}$ hydroxyalkyl, $C_{1-4}$ aminoalkyl, halogen, hydroxy, haloalkyl, haloalkoxy, amino, $C_{1-4}$ alkylamino, and/or cyano;

$R_{12}$, $R_{13}$, $R_{14}$, $R_{18}$, $R_{19}$, $R_{22}$ $R_{23}$, and $R_{24}$ are independently selected from hydrogen, alkyl, substituted alkyl, alkenyl, substituted alkenyl, aryl, heteroaryl, cycloalkyl, and heterocyclo;

$R_{15}$, $R_{20}$ and $R_{21}$ are independently selected from alkyl, substituted alkyl, alkenyl, substituted alkenyl, aryl, heteroaryl, cycloalkyl, and heterocyclo; $R_{16}$ is alkyl, substituted alkyl, alkenyl, substituted alkenyl, aryl, heteroaryl, cycloalkyl, or heterocyclo;

$R_{25}$ at each occurrence is selected from $C_{1-4}$alkyl, $C_{1-4}$alkoxy, $C_{1-4}$hydroxyalkyl, $C_{1-4}$aminoalkyl, halogen, hydroxy, haloalkyl, haloalkoxy, amino, $C_{1-4}$alkylamino, and/or cyano;

p is 1 or 2;

q is 1, 2 or 3; and u is 1 or 2;

provided that when Z is phenyl, pyridyl or pyridazinyl, $R_9$, $R_{10}$ and/or $R_{11}$ are other than cyano or —C(=NR$_{22}$)NR$_{23}$R$_{24}$.

More preferred compounds are those having the formula (Ia), as recited above, or a stereoisomer or pharmaceutically-acceptable salts, hydrates, or prodrugs thereof, wherein:

X is selected from —OH, —O(phenyl), —O(benzyl), —NH(phenyl), and wherein each phenyl or benzyl group is optionally subsituted with one to two $R_{25}$, W is hydrogen or —(CH$_2$)$_q$—H;

Z is selected from

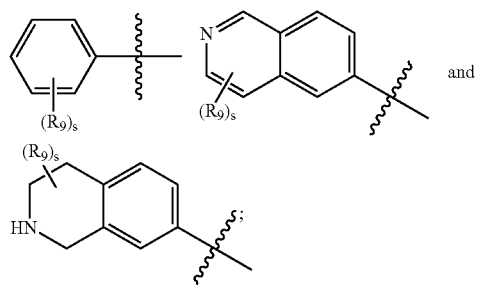

$R_1$ and $R_2$ are OR$_{12}$;

$R_9$ is selected from hydrogen, halogen, alkyl, substituted alkyl, haloalkyl, haloalkoxy, cyano, nitro, —S(O)$_u$R$_{21}$, —NR$_{22}$SO$_2$R$_{21}$, —C(=O)NR$_{22}$R$_{23}$, —OR$_{22}$, —CO$_2$R$_{22}$, —C(=O)R$_{22}$, —SR$_{22}$, —NR$_{22}$R$_{23}$, —NR$_{22}$CO$_2$R$_{23}$, —NR$_{22}$C(=O)R$_{23}$, —NR$_{22}$C(=O)NR$_{23}$R$_{24}$, —SO$_2$NR$_{22}$R$_{23}$, —NR$_{22}$SO$_2$NR$_{23}$R$_{24}$, five or six membered heterocyclo or heteroaryl, phenyl, and $C_{3-7}$cycloalkyl;

$R_{12}$, $R_{22}$, $R_{23}$ and $R_{24}$ are selected from hydrogen, alkyl, substituted alkyl, alkenyl, substituted alkenyl, aryl, heteroaryl, cycloalkyl, or heterocyclo;

$R_{21}$ is selected from alkyl, substituted alkyl, alkenyl, substituted alkenyl, aryl, heteroaryl, cycloalkyl, and heterocyclo;

$R_{25}$ at each occurrence is selected from $C_{1-4}$alkyl, $C_{1-4}$alkoxy, $C_{1-4}$hydroxyalkyl, $C_{1-4}$aminoalkyl, halogen, hydroxy, haloalkyl, haloalkoxy, amino, $C_{1-4}$alkylamino, and/or cyano;

q is 1, 2 or 3;

s is 0, 1, or 2; and u is 1 or 2;

provided that when Z is phenyl, $R_9$ and/or $R_{11}$ are other than cyano or —C(=NR$_{22}$)NR$_{23}$R$_{24}$.

More preferred are compounds having the formula (Ib),

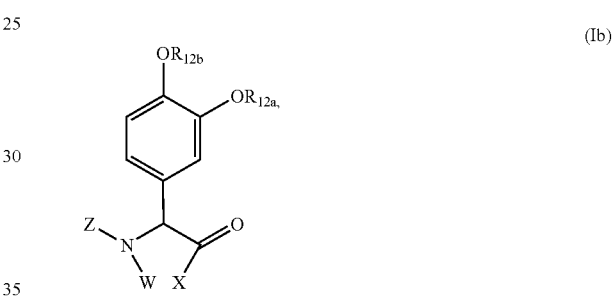

or a stereoisomer or pharmaceutically-acceptable salts, hydrates, or prodrugs thereof, wherein:

X is selected from —O(phenyl), —O(benzyl), and —NH(phenyl) —NH(benzyl), wherein each group X is optionally subsituted with one to two $R_{25}$, W is hydrogen or —(CH$_2$)$_q$—H;

Z is selected from

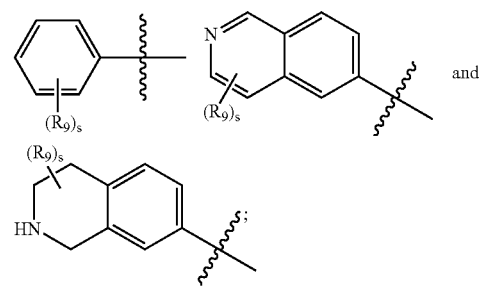

$R_9$ is independently selected from hydrogen, halogen, alkyl, aminoalkyl, hydroxyalkyl, haloalkyl, haloalkoxy, alkoxy, cyano, nitro, alkylamino, alkylthio, thioalkyl, —C(=O)NH$_2$, —C(=O)NH(C$_{1-4}$alkyl), —C(=O)N(C$_{1-4}$alkyl)$_2$, five or six membered heterocyclo or heteroaryl, phenyl, and $C_{3-7}$cycloalkyl;

$R_{12a}$ and $R_{12b}$ are independently selected from hydrogen, alkyl, substituted alkyl, phenyl, and benzyl;

$R_{25}$ at each occurrence is selected from $C_{1-4}$alkyl, $C_{1-4}$alkoxy, $C_{1-4}$hydroxyalkyl, $C_{1-4}$aminoalkyl, halogen, hydroxy, haloalkyl, haloalkoxy, amino, $C_{1-4}$alkylamino, and/or cyano;

p is 1 or 2; and s is 0, 1 or 2;

provided that when Z is phenyl, $R_9$ and/or $R_{11}$ are other than cyano or $-C(=NR_{22})NR_{23}R_{24}$.

More preferred are compounds as immediately defined above wherein:

$R_{12a}$ and $R_{12b}$ are selected from $C_{1-4}$alkyl; and

Z is selected from:

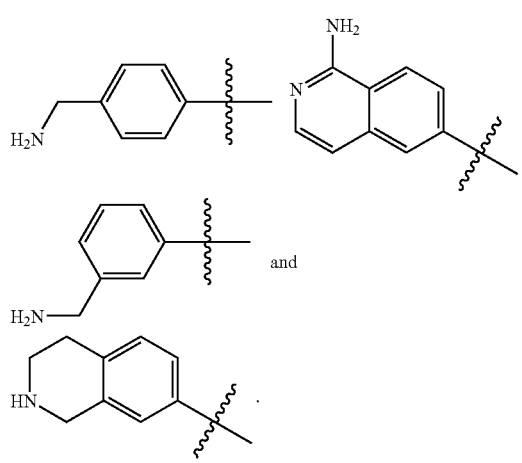

More preferred compounds are those having the formula (I), wherein:

Z is selected from:

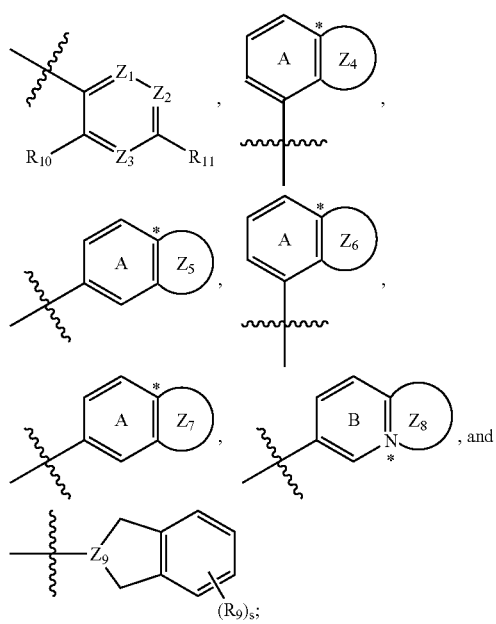

$Z_4$ is fused to ring A comprising the common carbon atom $C^*$ and is

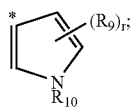

$Z_5$ is fused to ring A comprising the common carbon atom $C^*$ and is selected from:

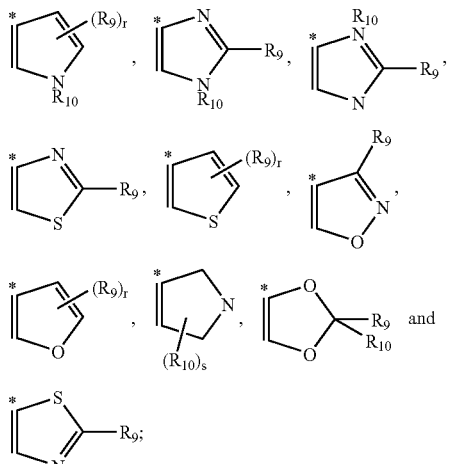

$Z_6$ is fused to ring A comprising the common carbon atom $C^*$ and is

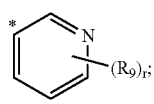

$Z_7$ is fused to ring A comprising the common carbon atom $C^*$ and is selected from:

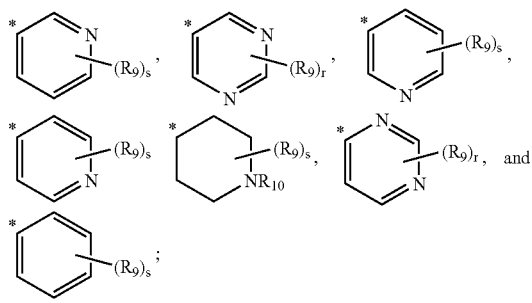

$Z_8$ is fused to ring B comprising the common nitrogen atom $N^*$ and is selected from

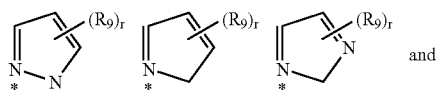

-continued
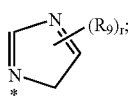
$Z_9$ is CH or N;
r is 0, 1, or 2; and
s is 0, 1, 2, or 3.
More preferred compounds are those having the formula (I), wherein:
Z is selected from:
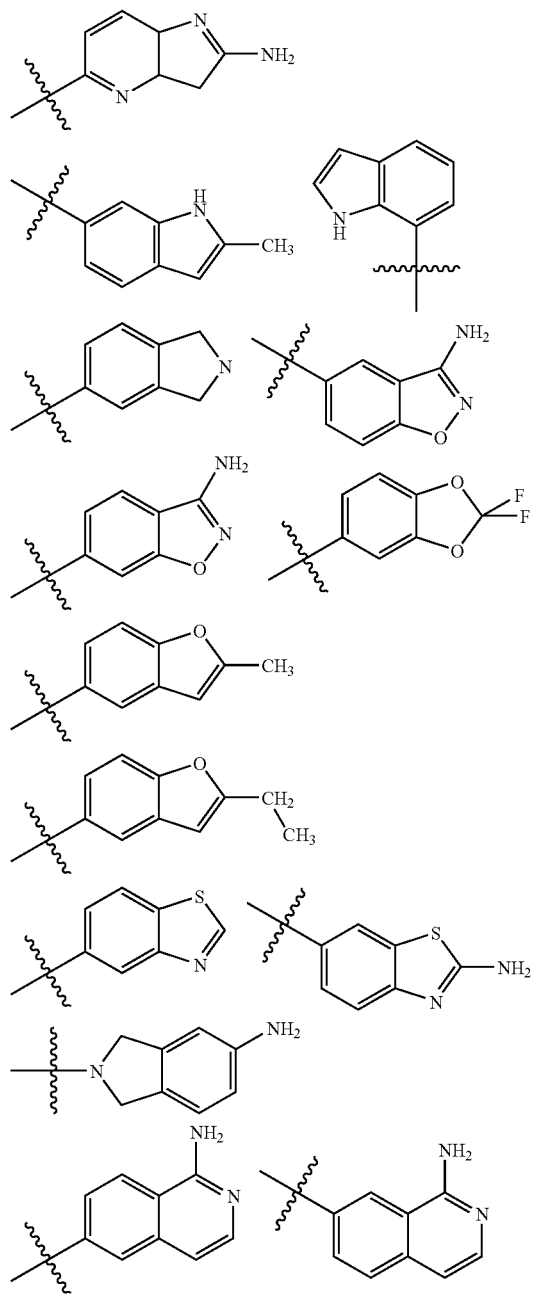
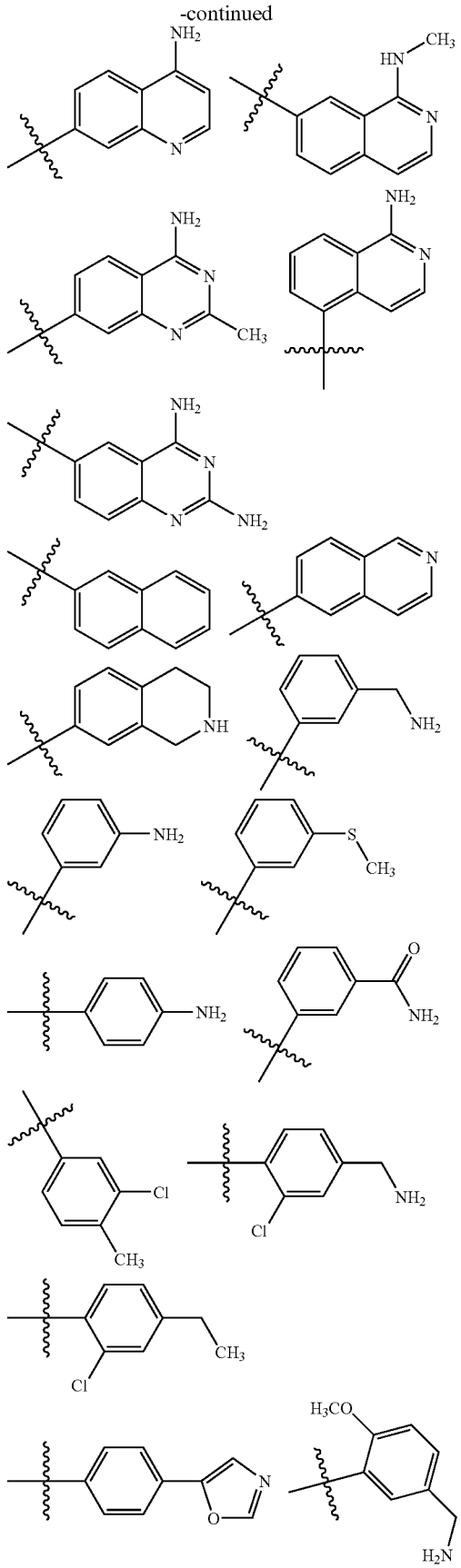

-continued

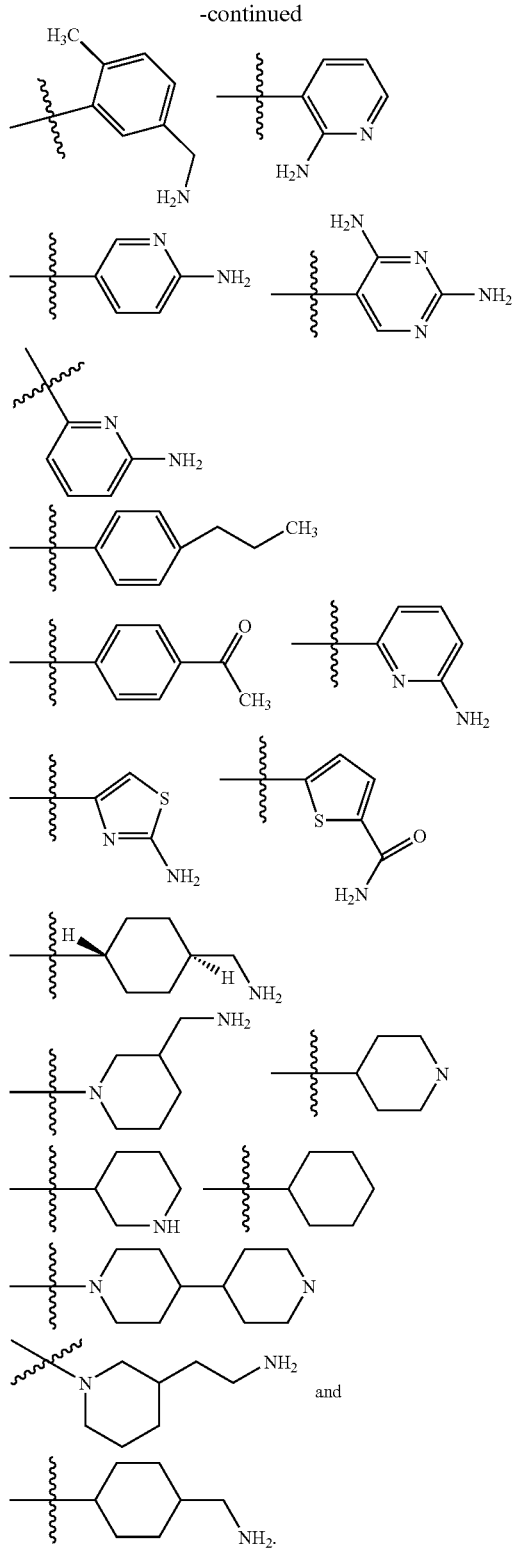

More preferred compounds are those having the formula (I), wherein:

R$_1$ and R$_2$ are OR$_{12}$.

More preferred compounds are those having the formula (I), wherein:

wherein R$_{12}$ is C$_{1-6}$alkyl, phenyl, or benzyl optionally substituted with one to two of halogen, cyano, haloalkyl, haloalkoxy, nitro, hydroxy, C$_{1-4}$alkyl, C$_{1-4}$hydroxyalkyl, C$_{1-4}$alkoxy, amino, NH(C$_{1-4}$alkyl), and N(C$_{1-4}$alkyl)$_2$.

More preferred compounds are those having the formula (I), wherein:

wherein W is hydrogen.

More preferred compounds are those having the formula (I), wherein:

X is NH(phenyl), NH(benzyl), SO$_2$alkyl, or SO$_2$(phenyl) optionally substituted with one to two of C$_{1-4}$alkyl, C$_{1-4}$alkoxy, C$_{1-4}$hydroxyalkyl, C$_{1-4}$aminoalkyl, halogen, hydroxy, haloalkyl, haloalkoxy, amino, C$_{1-4}$alkylamino, and/or cyano.

More preferred compounds are those having the formula (Ib), wherein:

X is selected from —O(phenyl) optionally substituted with one to two R$_{25}$, —O(benzyl) optionally substituted with one to two R$_{25}$, —NH(phenyl) optionally substituted with one to two R$_{25}$, and —NH(phenylalkyl) optionally substituted with one to two R$_{25}$;

W is hydrogen or —(CH$_2$)$_q$—H;

Z is selected from:

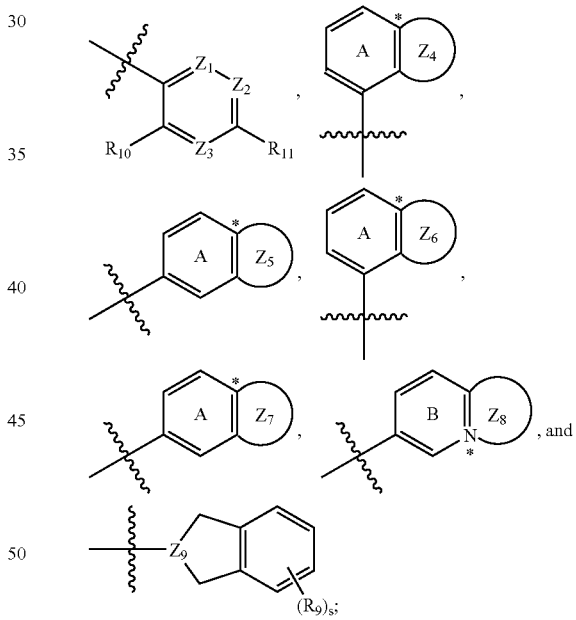

Z$_1$, Z$_2$ and Z$_3$ are selected from N and CR$_9$;

Z$_4$ is fused to ring A comprising the common carbon atom C* and is

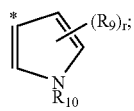

Z$_5$ is fused to ring A comprising the common carbon atom C* and is selected from:

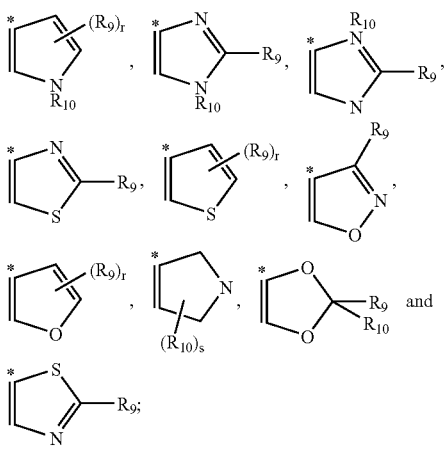

$Z_6$ is fused to ring A comprising the common carbon atom C* and is

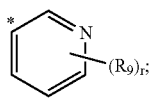

$Z_7$ is fused to ring A comprising the common carbon atom C* and is selected from:

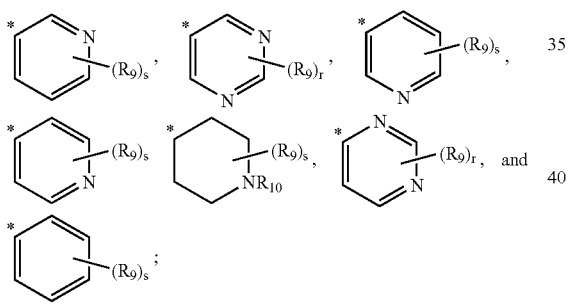

$Z_8$ is fused to ring B comprising the common nitrogen atom N* and is selected from

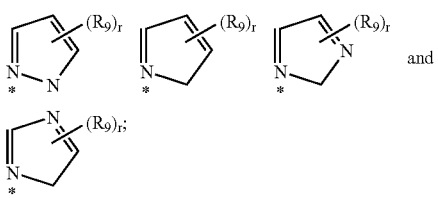

$Z_9$ is CH or N;

$R_9$ and $R_{10}$ are independently selected from hydrogen, halogen, alkyl, substituted alkyl, haloalkyl, haloalkoxy, cyano, nitro, —S(O)$_u$, $R_{21}$, —NR$_{22}$SO$_2$R$_{21}$, —C(=O)NR$_{22}$R$_{23}$, —OR$_{22}$, —CO$_2$R$_{22}$, —C(=O)R$_{22}$, —SR$_{22}$, —NR$_{22}$R$_{23}$, —NR$_{22}$CO$_2$R$_{23}$, —NR$_{22}$C(=O)R$_{23}$, —NR$_{22}$C(=O)NR$_{23}$R$_{24}$, —SO$_2$NR$_{22}$R$_{23}$, —NR$_{22}$SO$_2$NR$_{23}$R$_{24}$, —C(=NR$_{22}$)NR$_{23}$R$_{24}$, five or six membered heterocyclo or heteroaryl, phenyl, and C$_{3-7}$cycloalkyl, provided that $R_9$ and $R_{10}$ are not —C(=NR$_{22}$)NR$_{23}$R$_{24}$ when W is hydrogen; wherein when $R_9$ or $R_{10}$ is independently selected from heterocyclo, heteroaryl, phenyl, and C$_{3-7}$cycloalkyl, each of said cyclic groups in turn is optionally substituted with up to three of C$_{1-4}$alkyl, C$_{1-4}$alkoxy, C$_{1-4}$hydroxyalkyl, C$_{1-4}$aminoalkyl, halogen, hydroxy, haloalkyl, haloalkoxy, amino, C$_{1-4}$alkylamino, and/or cyano;

$R_{12}$, $R_{12a}$, $R_{12b}$, $R_{22}$ $R_{23}$, and $R_{24}$ are independently selected from hydrogen, alkyl, substituted alkyl, alkenyl, substituted alkenyl, aryl, heteroaryl, cycloalkyl, and heterocyclo;

$R_{21}$ is selected from alkyl, substituted alkyl, alkenyl, substituted alkenyl, aryl, heteroaryl, cycloalkyl, and heterocyclo;

$R_{25}$ at each occurrence is selected from C$_{1-4}$alkyl, C$_{1-4}$alkoxy, C$_{1-4}$hydroxyalkyl, C$_{1-4}$aminoalkyl, halogen, hydroxy, haloalkyl, haloalkoxy, amino, C$_{1-4}$alkylamino, and/or cyano;

p is 1 or 2;
q is 1, 2 or 3;
r is 0, 1, or 2;
s is 0, 1, 2, or 3;
t is 1 or 2; and
u is 1 or 2.

More preferred compounds are those having the formula (I), wherein:

X is NR$_5$(benzyl) optionally substituted with one to two $R_{25}$;
W is hydrogen;
Z is

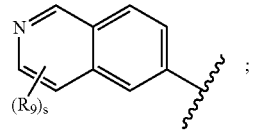

and $R_{25}$ at each occurrence is selected from halogen, cyano, nitro, C$_{1-10}$alkyl, C$_{2-10}$alkenyl, substituted C$_{1-10}$alkyl, substituted C$_{2-10}$alkenyl, —C(=O)NR$_{12}$R$_{13}$, —OR$_{12}$, —CO$_2$R$_{12}$, —C(=O)R$_{12}$, —SR$_{12}$, —S(O)$_t$R$_{15}$, —NR$_{12}$R$_{13}$, —NR$_{12}$SO$_2$R$_{15}$, —NR$_{14}$SO$_2$NR$_{12}$R$_{13}$, —NR$_{12}$CO$_2$R$_{13}$, —NR$_{12}$C(=O)R$_{13}$, —NR$_{14}$C(=O)NR$_{12}$R$_{13}$, —SO$_2$NR$_{12}$R$_{13}$, aryl, heteroaryl, cycloalkyl, and heterocyclo.

More preferred compounds are those having the formula (I), wherein:

Z is

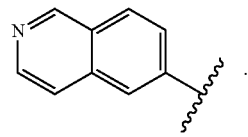

More preferred compounds are those having the formula (I), wherein:

Z is

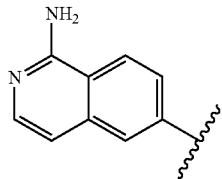

More preferred compounds are those having the formula (I), wherein:
X is OH;
W is hydrogen; and
Z is

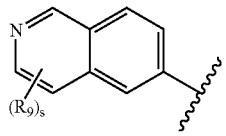

Methods of Preparation

The compounds of the invention may be prepared by the exemplary processes described in the following Schemes A through G.

SCHEME A

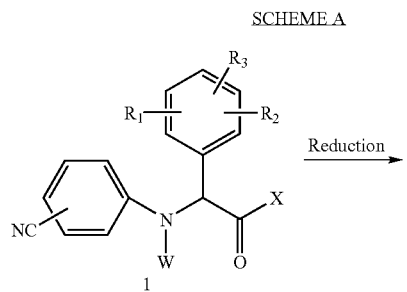

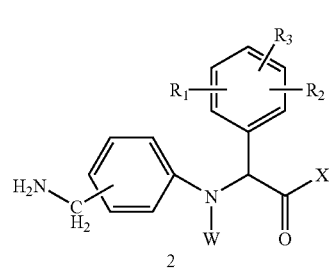

Compounds 2 [or compounds of formula (Ia)] can be prepared by reduction of the corresponding nitrile 1 using hydrogen and a catalyst such as Raney Nickel or Pd/C. The preparation of compounds 1 is described in U.S. Pat. No. 6,472,393.

SCHEME B

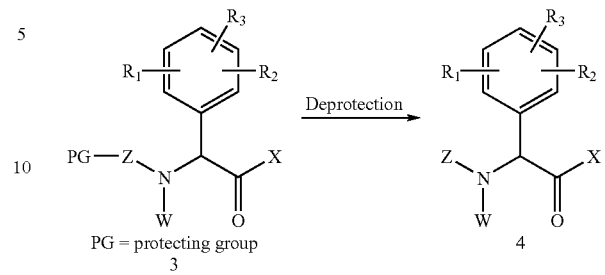

PG = protecting group

Compounds 4 are typically final products of formula (Ia). Compounds 4 were obtained by deprotection of a basic functionality in compound 3. Typical protecting group for a basic functionality are described in Green and Wuts, "*Protective Groups in Organic Synthesis, Second Edition*," John Wiley and Sons Eds, New York, (1991). Protecting group for amino or anilino groups include tert-butylcarbamate (Boc) which can be removed with a solution of TFA in DCM. Another protecting group for an amino or anilino group is 2,4-dimethoxybenzyl which can be removed by treatment with TFA in anisole or by catalytic hydrogenation. In the case of a primary amine or aniline, the nitrogen can be protected with one or two 2,4-dimethoxybenzyl groups. The first group can be removed with dilute TFA in an organic solvent while the second protecting can be removed with a 10–50% solution of TFA in anisole. Preparation of compounds of formula 3 is described in Schemes C–F.

SCHEME C

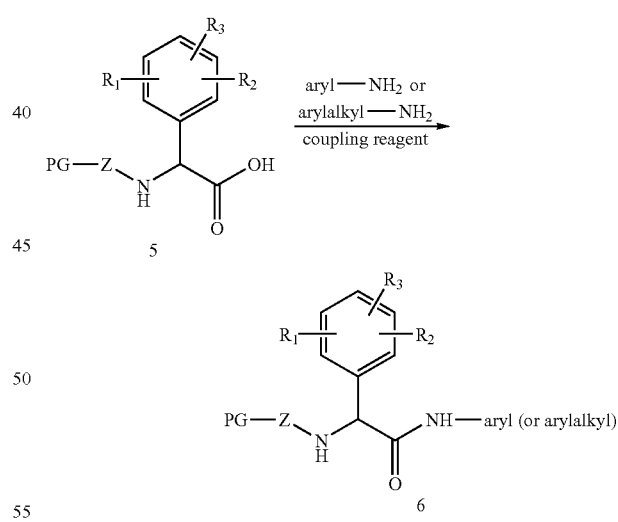

Amides 6 can be prepared from the corresponding carboxylic acids 5 by treatment with an amine and a coupling reagent. Coupling conditions can be found in Bodanszky, "Principles of Peptide Synthesis, Second Edition" Springer Verlag Ed, Berlin (1993). Coupling reagents include CDI, DIC, and EDC. Optionally, an intermediate activated ester can be prepared by adding one equivalent of 1-hydroxybenzotriazole or 1-hydroxy-7-azabenzotriazole. Other coupling reagents include HATU, HBTU, and Py-Brop which are usually reacted in presence of one equivalent of a tertiary base such as DIEA or TEA.

SCHEME D

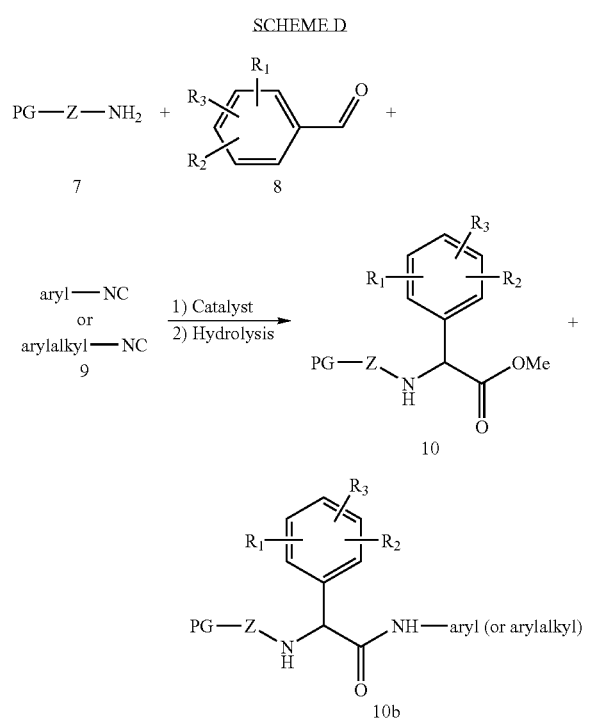

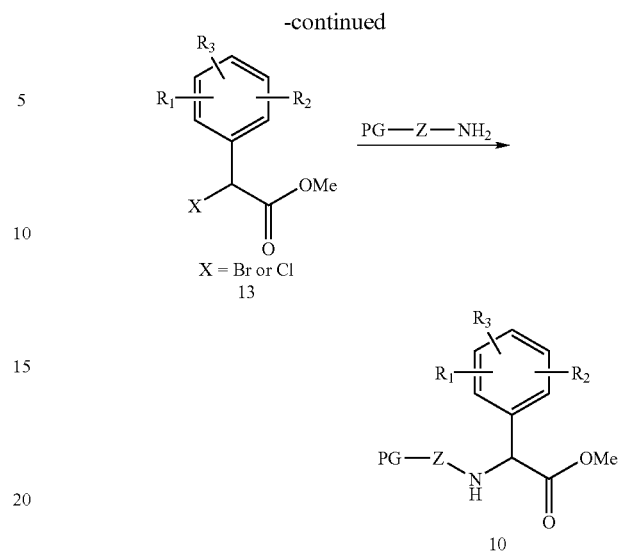

Compounds 10 and 10b can be prepared by a condensation reaction as described in U.S. Pat. No. 6,472,393. Reaction of an amine 7, with an aldehyde 8 and an isonitrile 9 in presence of a Lewis acid and an alkyl alcohol affords condensation product 10 after hydrolysis. Suitable Lewis acid catalysts include boron-trifluoride etherate or aluminium trichloride. Suitable alkyl alcohols include MeOH, EtOH, and I-PrOH. Examples of isonitrile 9 include benzyl isocyanide and tosylmethyl isocyanide. In some cases amides 10b were obtained as a side product in the reaction. These could be separated by column chromatography.

Alternatively to Scheme D, ester 10 can be prepared from hydroxy-ester 12. Compounds 12 can be prepared through a Strecker type synthesis, by condensation of an aldehyde 11 with trimethylsilylcyanide in presence of a Lewis acid catalyst such as Boron trifluoride etherate, followed by treatment with hydrochloric acid in MeOH and hydrolysis. Optionally, methyl ester 10 may be converted to the benzyl ester via saponification, followed by alkylation with benzyl bromide. Compounds 12 can be converted to 13 through one of the many halogenation methods known in the art. One suitable method is to treat the alcohol with a solution of bromine, triphenylphosphine and imidazole. Triphenylphosphine can be replaced with polystyrene bound triphenylphosphine which facilitates isolation of 13. Chlorination of compound 13 may be accomplished by treatment with methansulfonyl chloride and triethylamine in DCM. The halide 13 can be converted to 10 by nucleophilic substitution with an amine or aniline in an organic solvent such as DCM and in presence of a base such as TEA or DIPEA.

SCHEME E

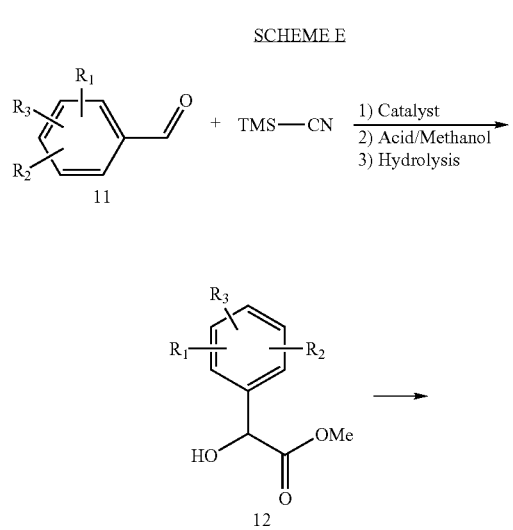

SCHEME F

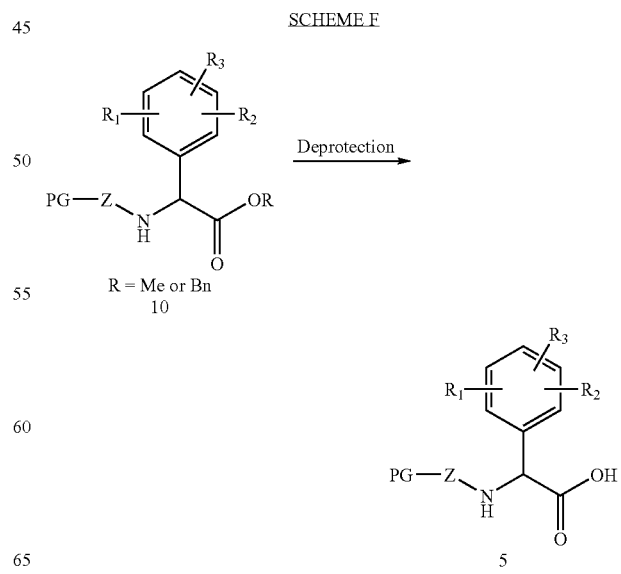

Saponification of methyl ester 10 to the corresponding carboxylic acids 5 can be accomplished using standard conditions well know in the art such as treatment with aqueous lithium hydroxide. Conversion of benzyl ester 10 to the carboxylic acids 5 can be accomplished via catalytic hydrogenation.
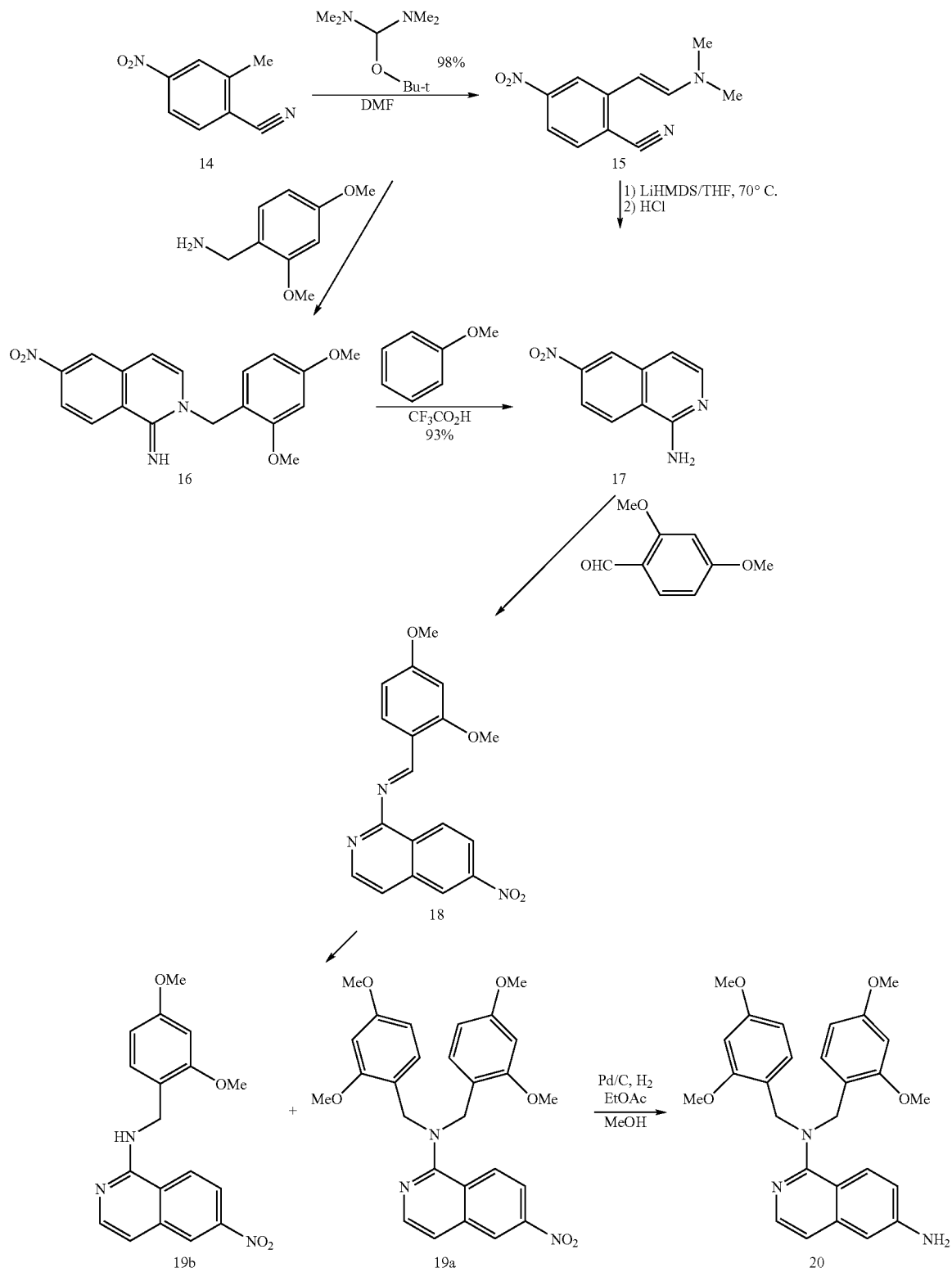

Scheme G described the preparation of reagent 20 (PG-Z-NH$_2$ where Z =1-aminoisoquinoline and PG=bis(2,4-dimethoxybenzyl) which can be used to make compounds of formula (I) by the methods described in Schemes A–F. Compound 15 was prepared, according to *J. Med. Chem.*, 1999, 42, 3510–3519, from 2-methyl-4-nitroaniline. A mixture of compound 14 and 1-(1,1-dimethylethoxy)-N,N,N',N'-tetramethyl-methanediamine in dry DMF (10 mL) was stirred at 70° C. for 2 h under N$_2$. After cooling to rt, the reaction mixture was treated with hexane, and the solid was collected by filtration and washed with hexane to give compound 15 as black crystals. Compound 15 was converted to compound 17 in two alternate ways.

In one approach, compound 15 was converted to 17 by adding IN LiHMDS to a solution of 15 in dry THF under N$_2$. The reaction mixture was stirred at 65° C. for 2 h. After cooling to rt, 12 N HCl was added and the reaction mixture stirred at 50° C. for 1 h. After cooling to rt, the mixture was neutralized with sat'd NaHCO$_3$, the product extracted with EtOAc, and the organic layer washed with water and sat'd NaCl. The product was concentrated and purified to give compound 17 as a yellow solid.

Alternatively, compound 15 was converted to 17 by first mixing compound 15 and 2,4-dimethoxylbenzylamine in DMF and stirring the mixture at 140° C. for 3 h. The solvent was removed by vacuum distillation and residue treated with EtOAc. The orange solid was collected by filtration and washed with hexane to give compound 16. To a solution of compound 16 in anisole was added TFA. The reaction mixture was stirred at 90° C. for 1 h and the solvent removed under reduced pressure. The residue was treated with sat'd NaHCO$_3$ (30 mL) and the product collected by filtration and washed with water to afford compound 17. Compound 23 (366 mg, 1.93 mmol) and 2,4-dimethoxybenzaldehyde were heated for 16 h at 125–130° C. with a stream of nitrogen passing in and out of the reaction flask, and sampling of the reaction mixture at 80° C. indicated conversion to compound 18.

To a solution of 18 and 2,4-dimethoxybenzaldehyde above in THF was added sodium triacetoxyborohydride. The reaction was stirred for 22 h and additional sodium triacetoxyborohydride (1.23 g, 5.8 mmol) was added. After 40 h, the reaction was concentrated to an oil which was taken up in EtOAc, water, and dilute sodium bicarbonate. The EtOAc was washed with water (3x), dried (sodium sulfate), and concentrated to an oily residue, which was purified to give compound 19a as a glassy residue and 140 mg of compound 19b as an amorphous solid. Hydrogenation of compound 19a in EtOAc and MeOH in the presence 10% Pd/C for 1 h at one atmosphere afforded compound 20 as an amorphous solid.

Utility

The inventive compounds are inhibitors of the activated coagulation serine protease Factor VIIa and are selective versus Factor IXa, Factor Xa, Factor XIa, and/or thrombin as well as other serine proteases such as trypsin, chymotrypsin, and urokinase. Thus, the compounds are useful for treating or preventing those processes which involve the action of Factor VIIa. As used herein, the term "treating" or "treatment" is intended to encompass responsive measures designed to cure the disease or disorder, to delay the progression of the disease or disorder, and/or to alleviate or lessen its symptoms, as well as prophylaxis measures designed to inhibit or delay the onset of the disease or disorder and/or its symptoms.

In view of their above-referenced serine protease inhibitory activity, the inventive compounds are useful in treating consequences of atherosclerotic plaque rupture including cardiovascular diseases associated with the activation of the coagulation cascade in thrombotic or thrombophilic states. Such diseases include arterial thrombosis, coronary artery disease, acute coronary syndromes, myocardial infarction, unstable angina, chronic stable angina, Prinzmetal's angina, ischemia resulting from vascular occlusion cerebral infarction, stroke and related cerebral vascular diseases (including cerebrovascular accident and transient ischemic attack). Additionally, the compounds are useful in treating or preventing formation of atherosclerotic plaques, transplant atherosclerosis, peripheral arterial disease and intermittent claudication. In addition, the compounds can be used to prevent restenosis following arterial injury induced endogenously (by rupture of an atherosclerotic plaque), or exogenously (by invasive cardiological procedures such as vessel wall injury resulting from angioplasty).

The inventive compounds are also useful in preventing venous thrombosis, coagulation syndromes, deep vein thrombosis (DVT), disseminated intravascular coagulopathy, pulmonary embolism, cerebral thrombosis, atrial fibrillation, and cerebral embolism. The compounds are useful in treating peripheral arterial occlusion, thromboembolic complications of surgery (such as hip replacement, endarterectomy, introduction of artificial heart valves, vascular grafts, and mechanical organs), implantation or transplantation of organ, tissue or cells, and thromboembolic complications of medications (such as oral contraceptives, hormone replacement, and heparin, e.g., for treating heparin-induced thrombocytopenia). The inventive compounds are useful in preventing thrombosis associated with artificial heart valves, stents, and ventricular enlargement including dilated cardiac myopathy and heart failure. The compounds are also useful in treating thrombosis due to confinement (i.e. immobilization, hospitalization, bed rest etc.).

These compounds are also useful in preventing thrombosis and complications in patients genetically predisposed to arterial thrombosis or venous thrombosis (including activated protein C resistance, FV$_{leiden}$, Prothrombin 20210, elevated coagulation factors FVII, FVIII, FIX, FX, FXI, prothrombin, TAFI and fibrinogen), elevated levels of homocystine, and deficient levels of antithrombin, protein C, and protein S. The inventive compounds may be used for treating heparin-intolerant patients, including those with congenital and acquired antithrombin III deficiencies, heparin-induced thrombocytopenia, and those with high levels of polymorphonuclear granulocyte elastase.

The present compounds may further be used to inhibit blood coagulation in connection with the preparation, storage, fractionation, or use of whole blood. For example, the compounds may be used to maintain whole and fractionated blood in the fluid phase such as required for analytical and biological testing, e.g., for ex vivo platelet and other cell function studies, bioanalytical procedures, and quantitation of blood-containing components. The compounds may be used as anticoagulants in extracorpeal blood circuits, such as those necessary in dialysis and surgery (such as coronary artery bypass surgery); for maintaining blood vessel patency in patients undergoing transluminal coronary angioplasty, vascular surgery including bypass grafting, arterial reconstruction, atherectomy, vascular graft and stent patency, tumor cell metastasis, and organ, tissue, or cell implantation and transplantation.

In a particular embodiment, compounds of the present invention are useful for treating any one or more of the aforementioned disorders irrespective of their etiology, e.g., for treating arterial thrombosis, coronary artery disease, acute coronary syndromes, myocardial infarction, unstable angina, ischemia, transplant rejection, rheumatoid arthritis, inflammatory bowel disease, and/or viral infections.

The present invention also provides pharmaceutical compositions comprising at least one compound of formula I, or a salt thereof, capable of treating a serine protease and/or a Factor-VIIa associated disorder, in an amount effective therefor, alone or in combination with at least one additional therapeutic agent, and a pharmaceutically acceptable carrier, adjuvant or vehicle. "Additional therapeutic agent" encompasses, but is not limited to, an agent or agents selected from the group consisting of immunosuppressants, potassium channel openers, calcium channel blockers, sodium hydrogen exchanger inhibitors, antiarrhythmic agents, antiatherosclerotic agents, anticoagulants such as antithrombotic agents (Factor Xa inhibitors, anti-platelet agents, or platelet aggregation inhibitors), prothrombolytic agents, fibrinogen antagonists, diuretics, anti-hypertensive agents, ATPase inhibitors, mineralocorticoid receptor antagonists, phospodiesterase inhibitors, antidiabetic agents, anti-inflammatory agents (steroidal and non-steroidal), antioxidants, angiogenesis modulators, antiosteoporosis agents, hormone replacement therapies or hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics (including thyroid receptor antagonists), anti-infective agents, antiviral agents, antibacterial agents, antifungal agents, cholesterol/lipid lowering agents and lipid profile therapies, and agents that mimic ischemic preconditioning and/or myocardial stunning.

In the methods of the present invention, such other therapeutic agent(s) may be administered prior to, simultaneously with or following the administration of the compound(s) of the present invention.

Examples of suitable other anti-inflammatory agents with which the inventive compounds may be used include aspirin, non-steroidal antiinflammatory drugs (NSAIDs) (such as ibuprofen and naproxin), TNF-α inhibitors (such as tenidap and rapamycin or derivatives thereof), or TNF-α antagonists (e.g., infliximab, OR1384), prednisone, dexamethasone, Enbrel®, cyclooxygenase inhibitors (i.e., COX-1 and/or COX-2 inhibitors such as Naproxen®, Celebrex®, or Vioxx®), CTLA4-Ig agonists/antagonists, CD40 ligand antagonists, IMPDH inhibitors, such as mycophenolate (CellCept®), integrin antagonists, alpha-4 beta-7 integrin antagonists, cell adhesion inhibitors, interferon gamma antagonists, ICAM-1, prostaglandin synthesis inhibitors, budesonide, clofazimine, CNI-1493, CD4 antagonists (e.g., priliximab), p38 mitogen-activated protein kinase inhibitors, protein tyrosine kinase (PTK) inhibitors, IKK inhibitors, therapies for the treatment of irritable bowel syndrome (e.g., Zelmac® and Maxi-K® openers such as those disclosed in U.S. Pat. No. 6,184,231), or other NF-κB inhibitors, such as corticosteroids, calphostin, CSAIDs, 4-substituted imidazo [1,2-A]quinoxalines as disclosed in U.S. Pat. No. 4,200,750; Interleukin-10, glucocorticoids, salicylates, nitric oxide, and other immunosuppressants; and nuclear translocation inhibitors, such as deoxyspergualin (DSG).

Examples of suitable other antibiotics with which the inventive compounds may be used include cyclosporins (e.g., cyclosporin A), CTLA4-Ig, antibodies such as anti-ICAM-3, anti-IL-2 receptor (Anti-Tac), anti-CD45RB, anti-CD2, anti-CD3 (OKT-3), anti-CD4, anti-CD80, anti-CD86, monoclonal antibody OKT3, agents blocking the interaction between CD40 and CD154 (a.k.a. "gp39"), such as antibodies specific for CD40 and/or CD154, fusion proteins constructed from CD40 and/or CD154/gp39 (e.g., CD40Ig and CD8gp39), β-lactams (e.g., penicillins, cephalosporins and carbopenams); β-lactam and lactamase inhibitors (e.g., augamentin); aminoglycosides (e.g., tobramycin and streptomycin); macrolides (e.g., erythromycin and azithromycin); quinolones (e.g., cipro and tequin); peptides and deptopeptides (e.g. vancomycin, synercid and daptomycin) metabolite-based antibiotics (e.g., sulfonamides and trimethoprim); polyring systems (e.g., tetracyclins and rifampins); protein synthesis inhibitors (e.g., zyvox, chlorophenicol, clindamycin, etc.); and nitro-class antibiotics (e.g., nitrofurans and nitroimidazoles).

Examples of suitable other antifungal agents with which the inventive compounds may be used include fungal cell wall inhibitors (e.g., candidas), azoles (e.g., fluoconazole and vericonazole), and membrane disruptors (e.g., amphotericin B). Examples of suitable other antiviral agents for use with the inventive compounds include nucleoside-based inhibitors, protease-based inhibitors, viral-assembly inhibitors, and other antiviral agents such as abacavir.

Other suitable therapeutic agents in combination with which the inventive compounds may be used include one or more of the following:

adenosine receptor modulators;

agents used to treat hypertension, heart failure, and/or atteroschlerosis, such as angiotensin-converting enzyme (ACE) inhibitors (e.g., captopril, lisinopril, zofenopril, ramipril, fosinopril, enalapril, ceranopril, cilazopril, delapril, pentopril, and quinapril), vasopeptidase inhibitors, i.e., dual ACE/NEP inhibitors (e.g., omapatrilat and gemopatrilat), AT-1 receptor antagonists (e.g., losartan, irbesartan, and valsartan), ET receptor antagonists (e.g., sitaxsentan, atrsentan, and compounds disclosed in U.S. Pat. Nos. 5,612,359 and 6,043,265), Dual ET/AII antagonists (e.g., compounds disclosed in WO 00/01389), neutral endopeptidase (NEP) inhibitors, and Rho-kinase inhibitors;

agents for inhibiting $F_1F_0$-ATPase, including efrapeptin, oligomycin, autovertin B, azide, and compounds described in WO 03/05026;

alpha- or beta-adrenergic blockers (such as propranolol, nadolol, carvedilol, and prazosin), or -β-adrenergic agonists (such as albuterol, terbutaline, formoterol, salmeterol, bitolterol, pilbuterol, and fenoterol);

angiogenesis modulators such as endostatin;

anotropic agents such as calcium channel blocking agents (t and 1) including verapamil, nifedipine, diltiazem, amlodipine, and mibefradil;

antianginal agents such as nitrates, for example, sodium nitrates, nitroglycerin, isosorbide mononitrate, isosorbide dinitrate, and nitrovisodilators;

antiarrhythmic agents including Class I agents (such as propafenone); Class II agents (propranolol); Class III agents (such as sotalol, dofetilide, amiodarone, azimilide and ibutilide); Class IV agents (such as ditiazem and verapamil); $K^+$ channel openers such as $I_{Ach}$ inhibitors and inhibitors of the $K_v1$ subfamily of $K^+$ channel openers such as $I_{Kur}$ inhibitors (e.g., compounds disclosed in U.S. Publication US 20030022890); and gap-junction modulators such as connexions;

anticholinergics such as ipratropium bromide;

anticoagulant or antithrombotic agents including aspirin, warfarin, ximelagtran, low molecular weight heparins (such as lovenox, enoxaparain, and dalteparin), anti-platelet agents such as GPIIb/GPIIIa blockers, (e.g., abciximab, eptifibatide, and tirofiban), thromboxane receptor antagonists (e.g., ifetroban), $P2Y_1$ and $P2Y_{12}$ antagonists (e.g., clopidogrel, ticlopidine, CS-747, and aspirin/clopidogrel combinations), and Factor Xa inhibitors (e.g., fondaparinux and razaxaban);

antidiabetic agents such as biguanides (e.g. metformin), glucosidase inhibitors (e.g. acarbose), insulins (including insulin secretagogues or insulin sensitizers), meglitinides (e.g. repaglinide), sulfonylureas (e.g., glimepiride, glyburide and glipizide), biguanide/glyburide combinations (e.g., glucovance), thiozolidinediones (e.g. troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in U.S. Pat. No. 6,548,529 assigned to the present assignee, glucagon-like peptide-1 (GLP-1), glucagon phosphorylase, and dipeptidyl peptidase IV (DP4) inhibitors;

antidepressant, antianxiety or antipsychotic agents such as nefazodone, sertraline, diazepam, lorazepam, buspirone, and hydroxyzine pamoate;

antioxidants and/or lipid peroxidation inhibitors such as probucol, BO-653, Vitamin A, Vitamin E, and AGI-1067;

antiosteoporosis agents such as alendronate and raloxifene;

antiobesity agents such as orlistat and aP2 inhibitors (such as those disclosed in U.S. Pat. No. 6,548,529;

antiproliferative agents such as cyclosporin A, paclitaxel, FK 506, and adriamycin;

antiulcer and gastroesophageal reflux disease agents such as famotidine, ranitidine, and omeprazole;

cardiac glycosides such as sodium calcium exchange inhibitors and digitalis;

diuretics such as sodium-hydrogen exchange inhibitors, chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, and amiloride;

hormone replacement therapies such as estrogen (e.g., congugated estrogens) and estradiol, and hormone receptor modulators such as androgen receptor modulators;

lipid profile modulators including HMG-CoA reductase inhibitors (e.g., pravastatin, simvastatin, atorvastatin, fluvastatin, cerivastatin, AZ4522, itavastatin [Nissan/Kowa]), ZD-4522 (a.k.a. rosuvastatin, atavastatin or visastatin), squalene synthetase inhibitors, fibrates, bile acid sequestrants (such as questran), niacin and niacin/statin combinations, ACAT1 inhibitors, ACAT2 inhibitors, dual ACAT1/2 inhibitors, microsomal triglyceride transport protein inhibitors (such as disclosed in U.S. Pat. Nos. 5,739,135, 5,712,279 and 5,760,246), cholesterol absorption inhibitors, cholesterol ester transfer protein inhibitors (e.g., CP-529414), PPAR-delta agonists, PPAR-alpha agonists, dual PPAR-alpha/delta agonists, LXR-alpha agonists, LXR-beta agonists, LXR dual alpha/beta agonists, and SCAP modulators;

mineralocorticoid receptor antagonists such as spironolactone and eplerenone;

phosphodiesterase (PDE) inhibitors that block the hydrolysis cAMP and/or cGMP including dipyridamole, cilostazol, sildenafil, rolipram, denbutyline, theophylline (1,2-dimethylxanthine), and ARIFLO™ (i.e., cis-4-cyano-4-[3-(cyclopentyloxy)-4-methoxyphenyl]cyclohexane-1-carboxylic acid), or PDE inhibitors in combination with anti-platelet agents;

prostacyclin mimetics such as berapist;

serotonin-2-receptor antagonists (such as ketanserin);

sodium hydrogen exchange-1 (NHE-1) inhibitors such as cariporide and zoniporide;

thrombolytic agents such as tissue plasminogen activator (natural or recombinant), streptokinase, reteplase, activase, lanoteplase, urokinase, prourokinase, tenecteplase (TNK), lanoteplase (nPA), anisolated streptokinase plasminogen activator complex (ASPAC), animal salivary gland plasminogen activators, PAI-1 inhibitors such as XR-330 and T-686, procarboxy peptidase-U, TAFI inhibitors, and inhibitors of α-2-antiplasmin such as anti-α-2-antiplasmin antibody;

urotensin modulators; and vasopressin receptor antagonists.

The above other therapeutic agents, when employed in combination with the compounds of the present invention, may be used in the same dosage form with the compound of formula I, in different dosage forms, in those amounts indicated in the Physicians' Desk Reference (PDR), and/or as otherwise determined by one of ordinary skill in the art.

The compounds of the present invention may act in a synergistic fashion with one or more of the above agents to allow for increased efficacy and/or reduced doses of any of the above agents and therefore minimize potential side-effects such as potential hemorrhagic side effects.

The term "pharmaceutically acceptable carrier, adjuvant or vehicle" refers to a carrier, adjuvant or vehicle that may be administered to a subject, together with a compound of the present invention, and which does not destroy the pharmacological activity thereof. Pharmaceutically acceptable carriers, adjuvants and vehicles that may be used in the pharmaceutical compositions of the present invention include, but are not limited to, the following: ion exchangers, alumina, aluminum stearate, lecithin, self-emulsifying drug delivery systems ("SEDDS") such as d(-tocopherol polyethyleneglycol 1000 succinate), surfactants used in pharmaceutical dosage forms such as Tweens or other similar polymeric delivery matrices, serum proteins such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β- and γ-cyclodextrin, or chemically modified derivatives such as hydroxyalkylcyclodextrins, including 2- and 3-hydroxypropyl-β-cyclodextrins, or other solubilized derivatives may also be used to enhance delivery of the compounds of the present invention.

The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the formula I may be administered by any suitable means, for example, orally, such as in the form of tablets, capsules, granules or powders; sublingually; buccally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present compounds may also be administered liposomally.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The present compounds may also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

Exemplary compositions for rectal administration include suppositories which may contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

The effective amount of a compound of the present invention may be determined by one of ordinary skill in the art, and includes exemplary dosage amounts for an adult human of from about 0.1 to 500 mg/kg of body weight of active compound per day, which may be administered in a single dose or in the form of individual divided doses, such as from 1 to 5 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to Factor-VIIa associated disorders.

Factor VIIA Assay

The effectiveness of compounds of the present invention as inhibitors of the coagulation factor VIIa, as well as selectivity versus factors Ixa, Xa, XIa, or thrombin, can be determined using a relevant purified serine protease, respectively, and an appropriate synthetic substrate. The rate of hydrolysis of the chromogenic substrate by the relevant serine protease was measured both in the absence and presence of compounds of the present invention. Hydrolysis of the substrate resulted in the release of pNA (para-nitroaniline), which was monitored spectrophotometrically by measuring the increase in absorbance at 405 nM, or the release of AMC (amino methylcoumarin, which was monitored spectrofluorometrically by measuring the increase in emission at 460 nM with excitation at 380 nM. A decrease in the rate of absorbance change at 405 nM in the presence of inhibitor is indicative of enzyme inhibition. Such methods are known to one skilled in the art. The results of this assay are expressed as inhibitory constant, $K_i$.

Factor VIIa determinations were made in 0.005 M calcium chloride, 0.15 M sodium chloride, 0.05 M HEPES buffer containing 0.5% PEG 8000 at a pH of 7.4. Determinations were made using purified human Factor VIIa (Haematologic Technologies) or recombinant human Factor VIIa (Novo Nordisk) at a final assay concentration of 2–5 nM, recombinant soluble tissue factor at a concentration of 18–35 nM and the synthetic substrate H-D-Ile-Pro-Arg-pNA (S-2288; Chromogenix or BMPM-2; AnaSpec) at a concentration of 0.001 M. Compounds tested in the assay for Factor VIIa are considered to be active if they exhibit a $K_i$ of equal to or less than 25 μM. Preferred compounds of the present invention have $K_i$'s of equal to or less than 1 μM. More preferred compounds of the present invention have $K_i$'s of equal to or less than 0.1 μM. Even more preferred compounds of the present invention have $K_i$'s of equal to or less than 0.01 μM. Compounds of the present invention have demonstrated $K_i$ values of equal to or less than 25 μM in the assay for Factor VIIa, thereby confirming the utility of the compounds of the present invention as effective inhibitors of coagulation factor VIIa and as anticoagulants for treatment of thromboembolic disorders.

Factor IXa determinations were made in 0.005 M calcium chloride, 0.1 M sodium chloride, 0.05 M TRIS base and 0.5% PEG 8000 at a pH of 7.4. Determinations were made using purified human Factor IXa (Haematologic Technologies) at a final assay concentration of 20–100 nM and the synthetic substrate PCIXA2100-B (CenterChem) or Pefafluor IXa 3688 (H-D-Leu-Phe-Gly-Arg-AMC; CenterChem) at a concentration of 0.0004–0.0005 M. Compounds tested in the Factor IXa assay are considered to be active if they exhibit a $K_i$ of equal to or less than 25 μM.

Factor Xa determinations were made in 0.1 M sodium phosphate buffer at a pH of 7.4 containing 0.2 M sodium chloride and 0.5% PEG 8000. Determinations were made using purified human Factor Xa (Haematologic Technologies) at a final assay concentration of 150–1000 pM and the synthetic substrate S-2222 (Bz-Ile-Glu(gamma-OMe, 50%)-Gly-Arg-pNA; Chromogenix) at a concentration of 0.0002–0.0003 M. Compounds tested in the Factor Xa assay are considered to be active if they exhibit a $K_i$ of equal to or less than 25 μM.

Factor XIa determinations were made in 50 mM HEPES buffer at pH 7.4 containing 145 mM NaCl, 5 mM KCl, and 0.1% PEG 8000 (polyethylene glycol; JT Baker or Fisher Scientific). Determinations were made using purified human Factor XIa at a final concentration of 75–200 pM (Haematologic Technologies) and the synthetic substrate S-2366 (pyroGlu-Pro-Arg-pNA; Chromogenix) at a concentration of 0.0002–0.00025 M. Compounds tested in the Factor XIa assay are considered to be active if they exhibit a $K_i$ of equal to or less than 25 μM.

Thrombin determinations were made in 0.1 M sodium phosphate buffer at a pH of 7.4 containing 0.2 M sodium chloride and 0.5% PEG 8000. Determinations were made using purified human alpha thrombin (Haematologic Technologies or Enzyme Research Laboratories) at a final assay concentration of 200–250 pM and the synthetic substrate S-2366 (pyroGlu-Pro-Arg-pNA; Chromogenix) at a concentration of 0.0002 M. Compounds tested in the thrombin assay are considered to be active if they exhibit a $K_i$ of equal to or less than 25 μM.

The Michaelis constant, $K_m$, for substrate hydrolysis by each protease was determined at 25° C. using the method of Lineweaver and Burk. Values of $K_i$ were determined by allowing the protease to react with the substrate in the presence of the inhibitor. Reactions were allowed to go for periods of 20–180 minutes (depending on the protease) and the velocities (rate of absorbance change vs time) were measured. The following relationship was used to calculate $K_i$ values:

$(v_O - v_S)/v_S = I/(K_i(1+S/K_m))$ for a competitive inhibitor with one binding site; or $v_S/v_O = A + ((B-A)/1+((IC_{50}/(I)^n)))$ and
$K_i = IC_{50}/(1+S/K_m)$ for a competitive inhibitor where:
$v_O$ is the velocity of the control in the absence of inhibitor;
$v_S$ is the velocity in the presence of inhibitor;
I is the concentration of inhibitor;
A is the minimum activity remaining (usually locked at zero);
B is the maximum activity remaining (usually locked at 1.0);

n is the Hill coefficient, a measure of the number and cooperativity of potential inhibitor binding sites;
$IC_{50}$ is the concentration of inhibitor that produces 50% inhibition under the assay conditions;
$K_i$ is the dissociation constant of the enzyme: inhibitor complex;
S is the concentration of substrate; and
$K_m$ is the Michaelis constant for the substrate.

The effectiveness of compounds of the present invention as inhibitors of the coagulation factor VIIa can be determined using relevant in vivo thrombosis models, including In Vivo Electrically-induced Carotid Artery Thrombosis Models and In Vivo Rabbit Arterio-venous Shunt Thrombosis Models.

In Vivo Electrically-induced Carotid Artery Thrombosis Model:

The antithrombotic effect of compounds of the present invention can be demonstrated in the electrically-induced carotid artery thrombosis (ECAT) model in rabbits. In this model, rabbits are anesthetized with a mixture of ketamine (50 mg/kg i.m.) and xylazine (10 mg/kg i.m.). A femoral vein and a femoral artery are isolated and catheterized. The carotid artery is also isolated such that its blood flow can be measured with a calibrated flow probe that is linked to a flowmeter. A stainless steel bipolar hook electrode is placed on the carotid artery and positioned caudally in relationship to the flow probe as a means of applying electrical stimulus. In order to protect the surrounding tissue, a piece of Parafilm is placed under the electrode.

Test compounds are considered to be effective as anticoagulants based on their ability to maintain blood flow in the carotid artery following the induction of thrombosis by an electrical stimulus. A test compound or vehicle is given as continuous intravenous infusion via the femoral vein, starting 1 h before electrical stimulation and continuing to the end of the test. Thrombosis is induced by applying a direct electrical current of 4 mA for 3 min to the external arterial surface, using a constant current unit and a d.c. stimulator. The carotid blood flow is monitored and the time to occlusion (decrease of blood flow to zero following induction of thrombosis) in minutes is noted. The change in observed blood flow is calculated as a percentage of the blood flow prior to induction of thrombosis and provides a measure of the effect of a test compound when compared to the case where no compound is administered. This information is used to estimate the $ED_{50}$ value, the dose that increases blood flow to 50% of the control (blood flow prior to induction of thrombosis) and is accomplished by nonlinear least square regression.

In Vivo Rabbit Arterio-venous Shunt Thrombosis Model:

The antithrombotic effect of compounds of the present invention can be demonstrated in a rabbit arterio-venous (AV) shunt thrombosis model. In this model, rabbits weighing 2–3 kg anesthetized with a mixture of xylazine (10 mg/kg i.m.) and ketamine (50 mg/kg i.m.) are used. A saline-filled AV shunt device is connected between the femoral arterial and the femoral venous cannulae. The AV shunt device consists of a piece of 6-cm tygon tubing that contains a piece of silk thread. Blood will flow from the femoral artery via the AV-shunt into the femoral vein. The exposure of flowing blood to a silk thread will induce the formation of a significant thrombus. After forty minutes, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The $ID_{50}$ values (dose which produces 50% inhibition of thrombus formation) are estimated by linear regression.

The following examples illustrate preferred embodiments of the present invention and do not limit the scope of the present invention which is defined in the claims. Abbreviations are employed in the Examples and Schemes set forth below for ease of reference as follows:

Abbreviations
  Me=methyl
  Et=ethyl
  MeOH=methanol
  EtOH=ethanol
  i-PrOH=isopropanol
  Ph=phenyl
  Bn=benzyl
  t-Bu=tertiary butyl
  Boc=tert-butoxycarbonyl
  AcOH=acetic acid
  i-Pr$_2$NEt=diisopropylethylamine
  CBZ=carbobenzyloxy or carbobenzoxy or benzyloxycarbonyl
  EtOAc=ethyl acetate
  CDI=carbonyl dimidazole
  DBU=1,8-Diazabicyclo[5.4.0]undec-7-ene
  DMF=dimethyl formamide
  DMSO=dimethyl sulfoxide
  DME=1,2 dimethoxyethane
  DCE=1,2 dichloroethane
  DCM=dichloromethane
  DMAP=4-dimethylaminopyridine
  DCC=dicyclohexylcarbodiimide
  DIC or DIPCDI=diisopropylcarbodiimide
  DIAD=diisopropyl azodicarboxylate
  DIPEA=diisopropylethylamine
  DPPF=1,1'-bis(diphenylphosphino)ferrocene
  DEPBT=3-(diethoxyphosphoryloxy)-1, 2, 3-benzotriazin-4(3H)-one
  DMB=2,4-dimethoxy-benzyl
  NMM=N-methyl morpholine
  NaHCO$_3$=sodium bicarbonate
  NaBH(OAc)$_3$=sodium triacetoxyborohydride
  EDC (or EDC.HCl) or EDCI (or EDCI.HCl) or EDAC=3-ethyl-3'-(dimethylamino)propyl-carbodiimide hydrochloride (or 1-(3-dimethylaminopropyl)-3-ethylcarbodiimide hydrochloride)
  HOBT or HOBT.H$_2$O=1-hydroxybenzotriazole hydrate
  HOAT=1-Hydroxy-7-azabenzotriazole
  HATU=[O-(7-azabenzotriazol-1-yl)-1,1,3,3-tetramethyluronium hexafluorophosphate
  HBTU=O-benzotriazol-1-yl-n,n,n',n'-tetramethyluronium hexafluorophosphate
  Py-Brop=bromo-tris-pyrolidino phosphonium hexafluorophosphate
  Pd/C=palladium on carbon
  Pd(OAc)$_2$=Palladium acetate
  SAX=Strong Anion Exchanger
  SCX=Strong Cation Exchanger
  PVP=polyvinylpyridine
  THF=tetrahydrofuran
  TFA=trifluoroacetic acid
  TEA=triethylamine
  TBS=t-butyldimethylsilyl
  Tf=trifluoromethanesulfonyl
  L=liter
  mL=milliliter
  μL=microliter
  g=gram(s)
  mg=milligram(s)
  meq=milliequivalent
  rt or RT=room temperature
  conc.=concentrated
  sat or sat'd=saturated
  TLC=thin layer chromatography
  HPLC=high performance liquid chromatography
  RP HPLC=reverse phase HPLC
  LC/MS=high performance liquid chromatography/mass spectrometry
  MS or Mass Spec=mass spectrometry
  MW=molecular weight
  mp=melting point

EXAMPLE 1

2-(4-Aminomethyl-phenylamino)-N-benzyl-2-(3-ethoxy-4-isopropoxy-phenyl)-acetamide

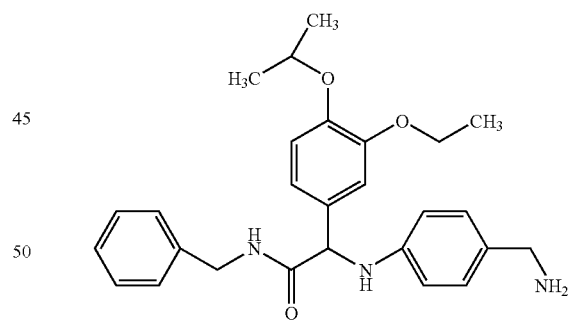

N-Benzyl-2-(4-cyano-phenylamino)-2-(3-ethoxy-4-isopropoxy-phenyl)-acetamide (150 mg, 0.34 mM) (prepared according to U.S. Pat. No. 6,472,393), was dissolved in 15 mL MeOH. Raney-Ni (30 mg) and AcOH (0.11 nL) were added. After Parr hydrogenation at 35 psi H$_2$ pressure for 48 h, the acetamide was consumed. After filtration and concentration the residue was dissolved in 2 mL dioxane/water (1:1), and HCl (100 μL, 1.0N aq. solution) was added. Lyophilation yielded the dihydrochloride salt of Example 2 (36 mg) as a white solid with a HPLC-purity of 82%. This material was further purified by prep-HPLC yielding 14 mg pure Example 1 (8.5%). LR-MS, M−H 446.2.

EXAMPLE 2

7-{[Carboxy-(3-ethoxy-4-isopropoxy-phenyl)-methyl]-amino}-3,4-dihydro-1H-isoquinoline-2-carboxylicacid tert-butyl ester

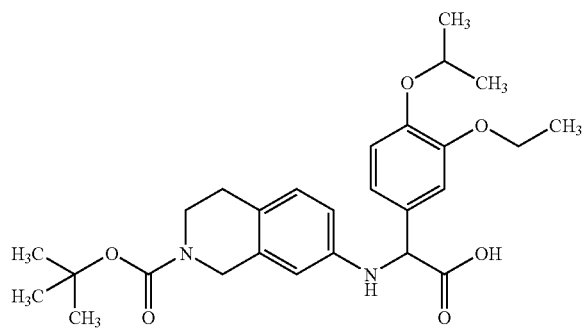

2A

7-{[(3-Ethoxy-4-isopropoxy-phenyl)-methoxycarbonyl-methyl]-amino}-3,4-dihydro-1H-isoquinoline-2-carboxylic acid tert-butyl ester

2A

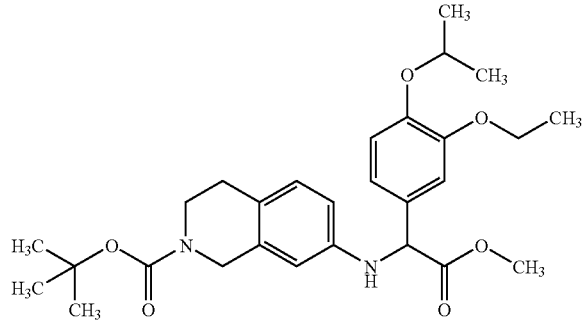

7-Amino-3,4-dihydro-1H-isoquinoline-2-carboxylic acid tert-butyl ester (99.33 mg, 0.40 mmol) and 3-ethoxy-4-isopropoxy-benzaldehyde (83.30 mg, 0.40 mmol) were dissolved into anhydrous MeOH (2.0 mL) and heated at 60° C. for 3.5 h. The mixture was cooled to rt and benzyl isonitrile (48.71 μL, 0.40 mmol) was added. The reaction was cooled to 0° C. and boron trifluoride diethyl etherate (152.07 μL, 1.20 mmol) was added in two aliquots. The reaction was allowed to warm to rt with shaking overnight. Water (60 μL) was added and the reaction was shaken at rt for one hour and concentrated. The residual oil was redissolved into EtOAc and washed with water (3×) and brine, dried over anhydrous $Na_2SO_4$, filtered, and concentrated. (The Boc protecting group fell off during the synthesis to give the free secondary amine.) The free amine product was captured on cation exchange resin and eluted off with ammonia in MeOH. The product was purified by preparative HPLC. The purified product (22.7 mg, 0.0570 mmol) was dissolved into anhydrous DCM (1.0 mL). TEA (9.54 μL, 0.0684 mmol) and DMAP (0.70 mg, 0.0057 mmol) were added. The reaction was cooled to 0° C. and di-tert-butyl dicarbonate (14.94 mg, 0.0684 mmol) was added. The reaction was allowed to warm to rt with shaking overnight and concentrated. The residue was dissolved into EtOAc and washed with sat'd $NaHCO_3$, water and brine, dried over anhydrous $Na_2SO_4$, filtered, and concentrated to yield 2A which was used in the subsequent step without further purification.

2B (EXAMPLE 2)

Compound 2A was dissolved into THF (1.5 mL). 2N LiOH (0.50 mL) was added. The reaction was vortexed at rt for 6.5 h. It was then concentrated to remove the THF. The residual oil was redissolved into water. Ice was added. This solution was acidified with 1N HCl and extracted with EtOAc. The combined EtOAc extracts were washed with water and brine, dried over anhydrous sodium sulfate, filtered and concentrated to yield 2B, Example 2.

EXAMPLE 3

[3-(tert-Butoxycarbonylamino-methyl)-phenylamino]-(3-ethoxy-4-isopropoxy-phenyl)-acetic acid

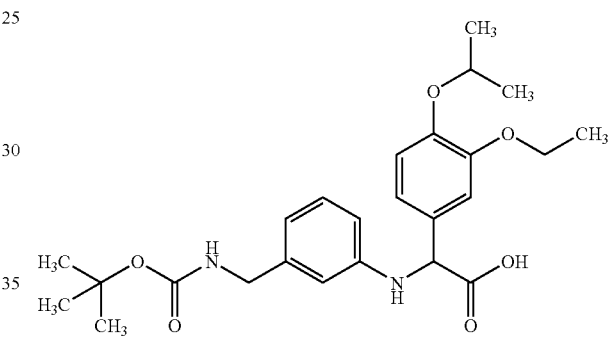

3A

[3-(tert-Butoxycarbonylamino-methyl)-phenylamino]-(3-ethoxy-4-isopropoxy-phenyl)-acetic acid methyl ester

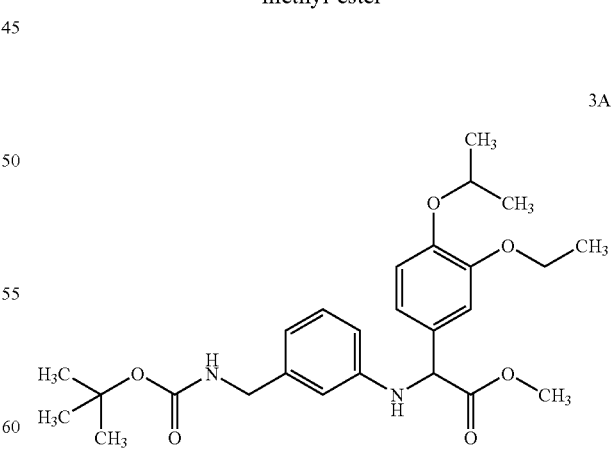

Compound 3A was prepared following the same or similar procedure as described above for 2A, except (3-aminobenzyl)-carbamic acid tert-butyl ester (88.91 mg, 0.40 mmol) was used instead of 7-amino-3,4-dihydro-1H-isoquinoline-2-carboxylic acid tert-butyl ester.

3B (EXAMPLE 3)

Compound 3B was prepared from 3A following the same or simliar procedure described above in 2B.

EXAMPLE 4

(1-Amino-isoquinolin-6-ylamino)-(3-ethoxy-4-isopropoxy-phenyl)-acetic acid

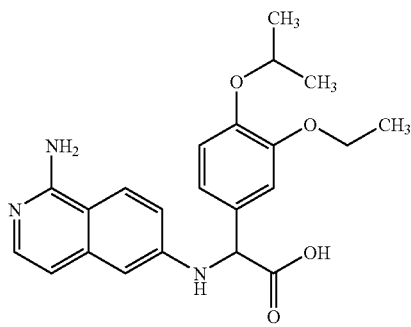

4A (3-Ethoxy-4-isopropoxy-phenyl)-hydroxy-acetic acid methyl ester

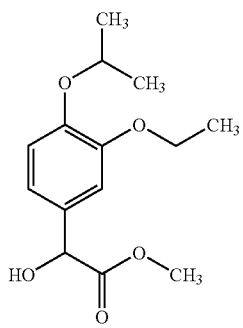

4A

To a solution of 3-ethoxy-4-isopropoxy-benzaldehyde (4.17 g, 20 mM) in DCM at −5° C. was added trimethylsilylcyanide (9.92 g, 0.1 M) followed by boron trifluoride etherate (1.0 mL). The solution was stirred for 4 days at rt. The reaction was monitored by consumption of 3-ethoxy-4-isopropoxy-benzaldehyde. The solution was concentrated in vacuo and the resulting oily residue was dissolved in dry ether (50 mL). MeOH (3.8 mL, 60 mM) was added followed by a solution of HCL in ether (60 mL of a 1.0M solution). The reaction solution was kept at −10° C. for 2 h and at 5° C. for 24 h. 4.44 g of white crystals formed which were filtered and washed with ether. The crystals were dissolved in water (25 mL) and DCM (25 mL) and stirred for 1 h at rt. The two phases were separated and the aqueous layer was extracted with DCM. The combined organic extracts were washed with brine, dried over sodium sulfate and concentrated to afford 3.52 g of compound 4A as a oil which crystallized to an off-white solid over several days.

4B

Bromo-(3-ethoxy-4-isopropoxy-phenyl)-acetic acid methyl ester

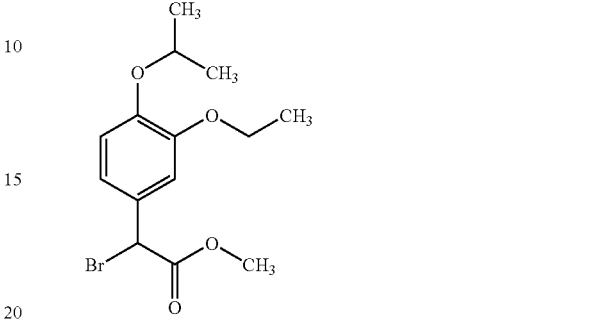

4B (3-Ethoxy-4-isopropoxy-phenyl)-hydroxy-acetic acid methyl ester 5A (100 mg, 0.37 mmol) was dissolved into anhydrous DCM (8.0 mL) and introduced into an oven-dried round bottom flask under argon. Resin bound triphenylphosphine (740 mg, 2.236 mmol), bromine (48 μL, 0.9269 mmol) and imidazole (26 mg, 0.3809 mmol) were added sequentially. The reaction was stirred at rt for 3 h. The resin was filtered off and washed with DCM. The filtrate was concentrated down. The resulting solid was triturated with diethyl ether. The insoluble solid was filtered away from the ethereal solution which was in turn concentrated down to yield 83 mg of 4B as a colorless oil of 52% purity by HPLC analysis. This material was used for the next step without further purification.

4C

{1-[Bis-(2,4-dimethoxy-benzyl)-amino]-isoquinolin-6-ylamino}-(3-ethoxy-4-isopropoxy-phenyl)-acetic acid methyl ester

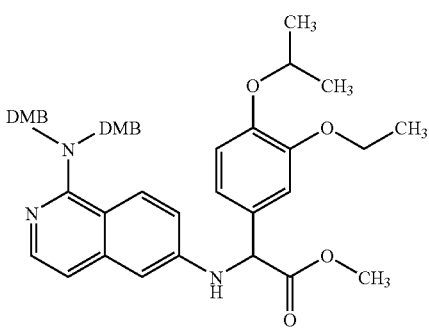

4C

A solution of N',N'-Bis-(2,4-dimethoxy-benzyl)-isoquinoline-1,6-diamine (38 mg, 0.0827 mmol) (compound 20, Scheme G), in anhydrous DCM (5 mL) was added to neat 4B (83 mg, 0.2506 mmol). DIEA (44 μL, 0.2506 mmol) was added and the reaction was stirred overnight at rt. The reaction mixture was concentrated to yield 123 mg of 4C a yellow oil which was purified by column chromatography on silica gel using 20–40% EtOAc in hexane.

4D

{1-[Bis-(2,4-dimethoxy-benzyl)-amino]-isoquinolin-6-ylamino}-(3-ethoxy-4-isopropoxy-phenyl)-acetic acid

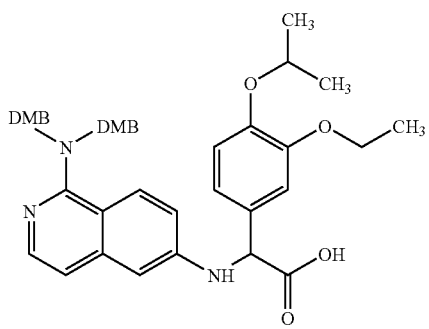

Compound 4C (22.2 mg) was dissolved in THF (1.5 mL). 2N LiOH (0.5 ml) was added, and the reaction mixture was stirred at RT for 4 h. The THF was evaporated. The residual oil was diluted with water and extracted with EtOAc. The basic aqueous solution was acidified to pH 1.0 with conc. HCl and extracted with EtOAc. The combined organic extracts were washed with water and brine, dried over anhydrous sodium sulfate, filtered and concentrated to afford 4D (18.9 mg, 87%) as a glassy yellow solid of 70% purity by LC/MS. This material was used in the next step without further purification.

4E (EXAMPLE 4)

Compound 4D (6.0 mg) was dissolved into anisole (0.20 ml) and cooled to 0° C. TFA (0.20 mL) was added. The reaction was stirred at 0° C. for 15 min and then quenched to pH 9 with TEA at 0° C. The reaction mixture was concentrated and the resulting oil was filtered through a C18 cartridge and then purified by preparative HPLC to afford the TFA salt of 4E (0.6 mg) as an orange oil ((M+H)+=396, HPLC Retention Time=2.42 min, column: Phenominex 4.6 mm×50 mm, 0–100% B 4 min gradient, Solvent A=10% MeOH–90% H$_2$O–10 mM NH$_4$Ac, Solvent B=90% MeOH–10% H$_2$O–10 mM NH$_4$Ac, 4 ml/min, Wavelength=220).

EXAMPLE 5

2-(1-Amino-isoquinolin-6-ylamino)-N-benzyl-2-(3-ethoxy-4-isopropoxy-phenyl)-acetamide

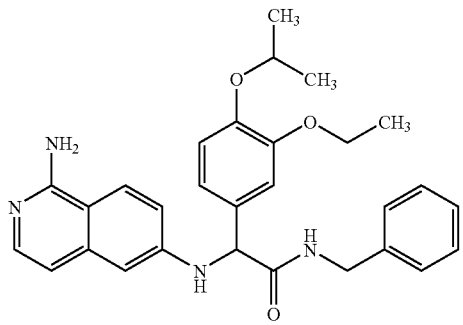

5A

N-Benzyl-2-{1-[bis-(2,4-dimethoxy-benzyl)-amino]-isoquinolin-6-ylamino}-2-(3-ethoxy-4-isopropoxy-phenyl)-acetamide

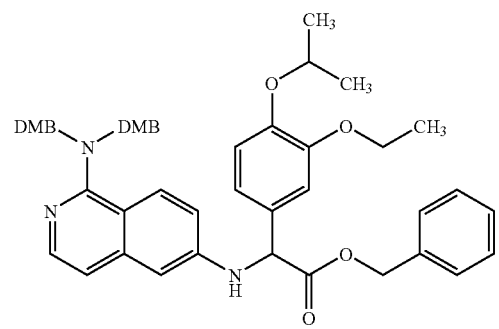

The carboxylic acid 4D (4.2 mg, 0.0060 mmol) was dissolved into anhydrous THF (0.50 mL). DEPBT (3.6 mg, 0.0120 mmol) and TEA (1.68 µL, 0.0120 mmol) were added. Benzylamine (0.98 µL, 0.0090 mmol) was added and the reaction mixture was stirred overnight at rt. The reaction mixture was concentrated down and used crude in the next step.

5B (EXAMPLE 5)

Compound 5A was treated with 1/1 TFA/anisole at 0° C. for 30 mins. The reaction was quenched with TEA and the mixture was filtered through a C18 cartridge. The filtrate was concentrated and the residue purified by preparative HPLC to afford the TFA salt of 5B (0.50 mg) as a colourless oil. ((M+H)+=485, HPLC Retention Time=3.06 min, column: Phenominex 4.6 mm×50 mm, 0–100% B 4 min gradient, Solvent A=10% MeOH–90% H$_2$O–10 mM NH$_4$Ac, Solvent B=90% MeOH–10% H$_2$O–10 mM NH$_4$Ac, 4 ml/min, Wavelength=220).

What is claimed is:

1. A compound according to formula (I),

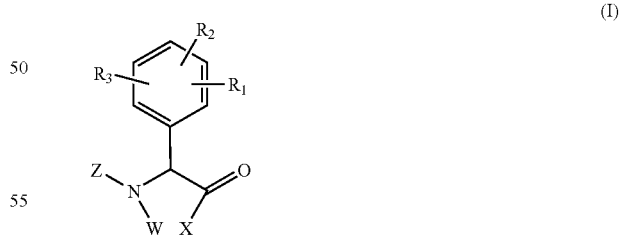

(I)

or a stereoisomer or a pharmaceutically-acceptable salt thereof, wherein:

X is —OH, —O(alkyl), —O(aryl), —O(arylalkyl), —NR$_5$(aryl), or —NR$_5$(arylalkyl);

wherein said aryl or arylalkyl are optionally substituted with one to two R$_{25}$;

W is hydrogen or —(CR$_7$R$_8$)$_q$—H;

Z is isoquinolyl optionally substituted with 1–3 substituents selected from R$_9$ and/or R$_{10}$;

$R_1$, $R_2$ and $R_3$ are attached to any available carbon atom of phenyl ring A and are independently selected from hydrogen, halogen, cyano, nitro, $C_{1-10}$alkyl, $C_{2-10}$alkenyl, substituted $C_{1-10}$alkyl, substituted $C_{2-10}$alkenyl, —C(=O)NR$_{12}$R$_{13}$, —OR$_{12}$, —CO$_2$R$_{12}$, —C(=O)R$_{12}$, —SR$_{12}$, —S(O)$_t$R$_{15}$, —NR$_{12}$R$_{13}$, —NR$_{12}$SO$_2$R$_{15}$, —NR$_{14}$SO$_2$NR$_{12}$R$_{13}$, —NR$_{12}$CO$_2$R$_{13}$, —NR$_{12}$C(=O)R$_{13}$, —NR$_{14}$C(=O)NR$_{12}$R$_{13}$, —SO$_2$NR$_{12}$R$_{13}$, aryl, heteroaryl, cycloalkyl, and heterocyclo;

$R_5$ is hydrogen, $C_{1-4}$alkyl, NH$_2$, $C_{1-4}$alkylamino, hydroxy, or $C_{1-4}$alkoxy;

$R_7$ and $R_8$ are independently selected from hydrogen, —OR$_{18}$, —NR$_{18}$R$_{19}$, —NR$_{18}$SO$_2$R$_{20}$, alkyl, alkenyl, substituted alkyl, substituted alkenyl, halogen, haloalkyl, haloalkoxy, cyano, nitro, alkylthio, —C(=O)H, acyl, —CO$_2$H, alkoxycarbonyl, sulfonamido, sulfonyl, and phenyl in turn optionally substituted with 1–3 of halogen, cyano, haloalkyl, haloalkoxy, nitro, hydroxy, $C_{1-4}$alkyl, $C_{1-4}$hydroxyalkyl, $C_{1-4}$alkoxy, amino, NH(C$_{1-4}$alkyl), N(C$_{1-4}$alkyl)$_2$, and/or $C_{1-4}$aminoalkyl;

$R_9$ and $R_{10}$ are independently selected from hydrogen, halogen, alkyl, substituted alkyl, haloalkyl, haloalkoxy, cyano, nitro, —S(O)$_u$R$_{21}$, —NR$_{22}$SO$_2$R$_{21}$, —C(=O)NR$_{22}$R$_{23}$, —OR$_{22}$, —CO$_2$R$_{22}$, —C(=O)R$_{22}$, —SR$_{22}$, —NR$_{22}$R$_{23}$, —NR$_{22}$CO$_2$R23, —NR$_{22}$C(=O)R$_{23}$, —NR$_{22}$C(=O)NR$_{23}$R$_{24}$, —SO$_2$NR$_{22}$R$_{23}$, —NR$_{22}$SO$_2$NR$_{23}$R$_{24}$, —C(=NR$_{22}$)NR$_{23}$R$_{24}$, five or six membered heterocyclo or heteroaryl, phenyl, and $C_{3-7}$cycloalkyl; wherein when $R_9$ or $R_{10}$ is selected from heterocyclo, heteroaryl, phenyl, and $C_{3-7}$cycloalkyl, each of said cyclic groups in turn is optionally substituted with up to three of $C_{4-1}$alkyl, $C_{1-4}$alkoxy, $C_{1-4}$ hydroxyalkyl, $C_{1-4}$aminoalkyl, halogen, hydroxy, haloalkyl, haloalkoxy, amino, $C_{1-4}$ alkylamino, and/or cyano;

$R_{12}$, $R_{13}$, $R_{14}$, $R_{18}$, $R_{19}$, $R_{22}$ $R_{23}$, and $R_{24}$ are independently selected from hydrogen, alkyl, substituted alkyl, alkenyl, substituted alkenyl, aryl, heteroaryl, cycloalkyl, and heterocyclo;

$R_{15}$, $R_{20}$ and $R_{21}$ are independently selected from alkyl, substituted alkyl, alkenyl, substituted alkenyl, aryl, heteroaryl, cycloalkyl, and heterocyclo;

$R_{25}$ at each occurrence is selected from hydrogen, halogen, cyano, nitro, $C_{1-10}$alkyl, $C_{2-10}$alkenyl, substituted $C_{1-10}$alkyl, substituted $C_{2-10}$alkenyl, —C(=O)NR$_{12}$R$_{13}$, —OR$_{12}$, —CO$_2$R$_{12}$, —C(=O)R$_{12}$, —SR$_{12}$, —S(O)$_t$R$_{15}$, —NR$_{12}$R$_{13}$, —NR$_{12}$SO$_2$R$_{15}$, —NR$_{14}$SO$_2$NR$_{12}$R$_{13}$, —NR$_{12}$CO$_2$R$_{13}$, —NR$_{12}$C(=O)R$_{13}$, —NR$_{14}$C(=O)NR$_{12}$R$_{13}$, —SO$_2$NR$_{12}$R$_{13}$, aryl, heteroaryl, cycloalkyl, and heterocyclo;

p is 1 or 2;

q is 1, 2 or 3;

t is 1 or 2; and u is 1 or 2.

2. A compound according to claim 1, or a stereoisomer or a pharmaceutically-acceptable salt thereof, wherein the compound is of formula (Ia):

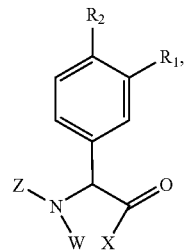

(Ia)

X is —OH, —O(phenyl) optionally substituted with one to two $R_{25}$, —O(benzyl) optionally substituted with one to two $R_{25}$, —NH(phenyl) optionally substituted with one to two $_{25}$, or NH(benzyl) optionally substituted with one to two $R_{25}$;

W is hydrogen or —(CH$_2$)$_q$—H;

Z is isoquinolyl optionally substituted with 1–3 substituents selected from $R_9$ and/or $R_{10}$.

$R_1$ and $R_2$ are independently selected from hydrogen, halogen, cyano, nitro, $C_{1-10}$alkyl, $C_{2-10}$alkenyl, substituted $C_{1-10}$alkyl, substituted $C_{2-10}$alkenyl, —C(=O)NR$_{12}$R$_{13}$, —OR$_{12}$, —CO$_2$R$_{12}$, —C(=O)R$_{12}$, —SR$_{12}$, —S(O)$_t$R$_{15}$, —NR$_{12}$R$_{13}$, —NR$_{12}$SO$_2$R$_{15}$, —NR$_{14}$SO$_2$NR$_{12}$R$_{13}$, —NR$_{12}$CO$_2$R$_{13}$, —NR$_{12}$C(=O)R$_{13}$, —NR$_{14}$C(=O)NR$_{12}$R$_{13}$, —SO$_2$NR$_{12}$R$_{13}$, aryl, heteroaryl, cycloalkyl, and heterocyclo;

$R_9$ and $R_{10}$ are independently selected from hydrogen, halogen, alkyl, substituted alkyl, haloalkyl, haloalkoxy, cyano, nitro, —S(O)$_u$R$_{21}$, —NR$_{22}$SO$_2$R$_{21}$, —C(=O)NR$_{22}$R$_{23}$, —OR$_{22}$, —CO$_2$R$_{22}$, —C(=O)R$_{22}$, —SR$_{22}$, —NR$_{22}$R$_{23}$, —NR$_{22}$CO$_2$R$_{23}$, —NR$_{22}$C(=O)R$_{23}$, —NR$_{22}$C(=O)NR$_{23}$R$_{24}$, —SO$_2$NR$_{22}$R$_{23}$, —NR$_{22}$SO$_2$NR$_{23}$R$_{24}$, —C(=NR$_{22}$)NR$_{23}$R$_{24}$, five or six membered heterocyclo or heteroaryl, phenyl, and $C_{3-7}$cycloalkyl; wherein when $R_9$ or $R_{10}$ is selected from heterocyclo, heteroaryl, phenyl, and $C_{3-7}$cycloalkyl, each of said cyclic groups in turn is optionally substituted with up to three of $C_{1-4}$alkyl, $C_{1-4}$alkoxy, $C_{14}$ hydroxyalkyl, $C_{1-4}$aminoalkyl, halogen, hydroxy, haloalkyl, haloalkoxy, amino, $C_{1-4}$ alkylamino, and/or cyano;

$R_{12}$, $R_{13}$, $R_{14}$, $R_{18}$, $R_{19}$, $R_{22}$ $R_{23}$, and $R_{24}$ are independently selected from hydrogen, alkyl, substituted alkyl, alkenyl, substituted alkenyl, aryl, heteroaryl, cycloalkyl, and heterocyclo;

$R_{15}$, $R_{20}$ and $R_{21}$ are independently selected from alkyl, substituted alkyl, alkenyl, substituted alkenyl, aryl, heteroaryl, cycloalkyl, and heterocyclo;

p is 1 or 2;

q is 1, 2 or 3; and u is 1 or 2.

3. A compound according to claim 2, wherein:

X is selected from —OH, —O(phenyl),—O(benzyl), —NH(phenyl), and wherein each phenyl or benzyl group is optionally subsituted with one to two $R_{25}$, W is hydrogen or —(CH$_2$)$_q$—H;

z is

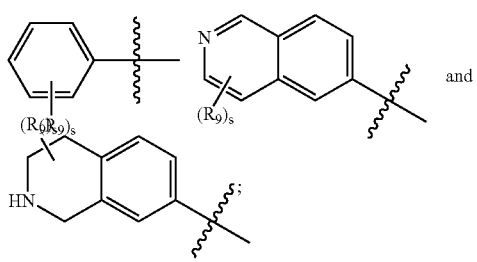

$R_1$ and $R_2$ are $OR_{12}$;

$R_9$ is selected from hydrogen, halogen, alkyl, substituted alkyl, haloalkyl, haloalkoxy, cyano, nitro, —S(O)$_u$R$_{21}$, —R$_{22}$SO$_2$R$_{21}$, —C(=O)NR$_{22}$R$_{23}$, —OR$_{22}$, —CO$_2$R$_{22}$, —C(=O)R$_{22}$, —SR$_{22}$, —NR$_{22}$R$_{23}$, —NR$_{22}$CO$_2$R$_{23}$, —NR$_{22}$C(=O)R$_{23}$, —NR$_{22}$C(=O)NR$_{23}$R$_{24}$, —SO$_2$NR$_{22}$R$_{23}$, —NR$_{22}$SO$_2$NR$_{23}$R$_{24}$, five or six membered heterocyclo or heteroaryl, phenyl, and C$_{3-7}$cycloalkyl;

$R_{12}$, $R_{22}$, $R_{23}$ and $R_{24}$ are selected from hydrogen, alkyl, substituted alkyl, alkenyl, substituted alkenyl, aryl, heteroaryl, cycloalkyl, or heterocyclo;

$R_{21}$ is selected from alkyl, substituted alkyl, alkenyl, substituted alkenyl, aryl, heteroaryl, cycloalkyl, and heterocyclo;

$R_{25}$ at each occurrence is selected from C$_{1-4}$alkyl, C$_{1-4}$alkoxy, C$_{1-4}$hydroxyalkyl, C$_{1-4}$aminoalkyl, halogen, hydroxy, haloalkyl, haloalkoxy, amino, C$_{1-4}$alkylamino, and/or cyano;

q is 1, 2 or 3;

s is 0, 1, or 2; and u is 1 or 2.

4. A compound according to claim 1, or a stereoisomer or a pharmaceutically-acceptable salt thereof, wherein the compound is of formula (Ib),

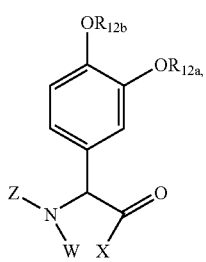

(Ib)

wherein:

X is selected from —O(phenyl), —O(benzyl), and —NH(phenyl) —NH(benzyl), wherein each group X is optionally subsituted with one to two R$_{25}$, W is hydrogen or —(CH$_2$)$_q$—H;

z is

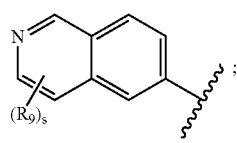

$R_9$ is independently selected from hydrogen, halogen, alkyl, aminoalkyl, hydroxyalkyl, haloalkyl, haloalkoxy, alkoxy, cyano, nitro, alkylamino, alkylthio, thioalkyl, —C(=O)NH$_2$, —C(=O)NH(C$_{1-4}$alkyl), —C(=O)N(C$_{1-4}$alkyl)$_2$, five or six membered heterocyclo or heteroaryl, phenyl, and C$_{3-7}$cycloalkyl;

$R_{12a}$ and $R_{12b}$ are independently selected from hydrogen, alkyl, substituted alkyl, phenyl, and benzyl;

$R_{25}$ at each occurrence is selected from C$_{1-4}$alkyl, C$_{1-4}$alkoxy, C$_{1-4}$hydroxyalkyl, C$_{1-4}$aminoalkyl, halogen, hydroxy, haloalkyl, haloalkoxy, amino, C$_{1-4}$alkylamino, and/or cyano;

p is 1 or 2; and s is 0, 1 or 2.

5. A compound according to claim 1, or a stereoisomer or a pharmaceutically-acceptable salt thereof, wherein Z is selected from:

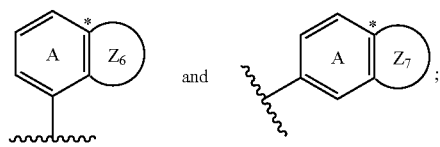

$Z_6$ is fused to ring A comprising the common carbon atom C* and is

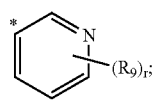

$Z_7$ is fused to ring A comprising the common carbon atom C* and is selected from:

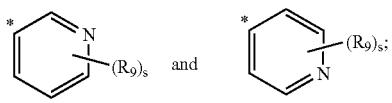

r is 0, 1, or 2; and s is 0, 1, 2, or 3.

6. A compound according to claim 1, or a stereoisomer or a pharmaceutically-acceptable salt thereof, wherein Z is selected from:

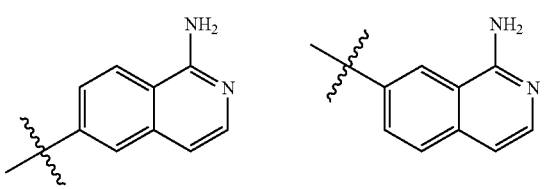

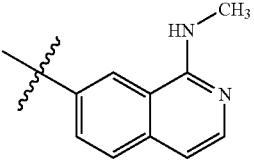

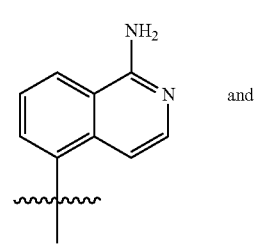

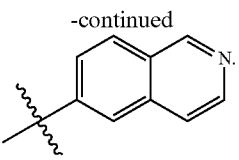

7. A compound according to claim 1, or a stereoisomer or a pharmaceutically-acceptable salt thereof, wherein $R_1$ and $R_2$ are $OR_{12}$.

8. A compound according to claim 7, or a stereoisomer or a pharmaceutically acceptable salt thereof, wherein $R_{12}$ is $C_{1-6}$alkyl, phenyl, or benzyl optionally substituted with one to two of halogen, cyano, haloalkyl, haloalkoxy, nitro, hydroxy, $C_{1-4}$alkyl, $C_{1-4}$hydroxyalkyl, $C_{1-4}$alkoxy, amino, $NH(C_{1-4}$alkyl), and $N(C_{1-4}$alkyl$)_2$.

9. A compound according to claim 8, or a stereoisomer or a pharmaceutically-acceptable salt thereof, wherein W is hydrogen.

10. A compound according to claim 9, or a stereoisomer or a pharmaceutically-acceptable salt thereof, wherein X is NH(phenyl), or NH(benzyl).

11. A compound having the formula (Ib),

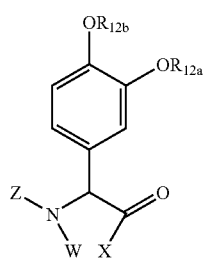

(Ib)

or a stereoisomer or a pharmaceutically-acceptable salt thereof, wherein:
X is selected from —O(phenyl) optionally substituted with one to two $R_{25}$, —O(benzyl) optionally substituted with one to two $R_{25}$, —NH(phenyl) optionally substituted with one to two $R_{25}$, and —NH(phenylalkyl) optionally substituted with one to two $R_{25}$;
W is hydrogen or —$(CH_2)_q$—H;
Z is selected from:

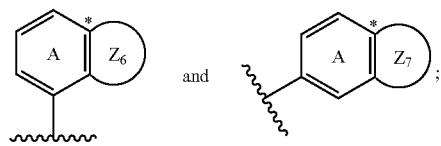

$Z_7$ is fused to ring A comprising the common carbon atom C* and is

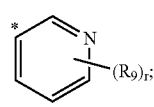

$Z_7$ is fused to ring A comprising the common carbon atom C* and is selected from:

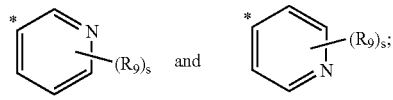

$R_9$ is independently selected from hydrogen, halogen, alkyl, substituted alkyl, haloalkyl, haloalkoxy, cyano, nitro, —S(O)$_u$R$_{21}$, —NR$_{22}$SO$_2$R$_{21}$, —C(=O)NR$_{22}$R$_{23}$, —OR$_{22}$, —CO$_2$R$_{22}$, —C(=O)R$_{22}$, —SR$_{22}$, —NR$_{22}$R$_{23}$, —NR$_{22}$CO$_2$R$_{23}$, —NR$_{22}$C(=O)R$_{23}$, —NR$_{22}$C(=O)NR$_{23}$R$_{24}$, —SO$_2$NR$_{22}$R$_{23}$, —NR$_{22}$SO$_2$NR$_{23}$R$_{24}$, five or six membered heterocyclo or heteroaryl, phenyl, and $C_{3-7}$cycloalkyl, provided that $R_9$ is not —C(=NR$_{22}$)NR$_{23}$R$_{24}$ when W is hydrogen; wherein when $R_9$ is independently selected from heterocyclo, heteroaryl, phenyl, and $C_{3-7}$cycloalkyl, each of said cyclic groups in turn is optionally substituted with up to three of $C_{1-4}$alkyl, $C_{1-4}$alkoxy, $C_{1-4}$hydroxyalkyl, $C_{1-4}$aminoalkyl, halogen, hydroxy, haloalkyl, haloalkoxy, amino, $C_{1-4}$alkylamino, and/or cyano;

$R_{12}$, $R_{12a}$, $R_{12b}$, $R_{22}$ $R_{23}$, and $R_{24}$ are independently selected from hydrogen, alkyl, substituted alkyl, alkenyl, substituted alkenyl, aryl, heteroaryl, cycloalkyl, and heterocyclo;

$R_{21}$ is selected from alkyl, substituted alkyl, alkenyl, substituted alkenyl, aryl, heteroaryl, cycloalkyl, and heterocyclo;

$R_{25}$ at each occurrence is selected from $C_{1-4}$alkyl, $C_{1-4}$alkoxy, $C_{1-4}$hydroxyalkyl, $C_{1-4}$aminoalkyl, halogen, hydroxy, haloalkyl, haloalkoxy, amino, $C_{1-4}$alkylamino, and/or cyano;

p is 1 or 2;
q is 1, 2 or 3;
r is 0, 1, or 2;
s is 0, 1, 2, or 3;
t is 1 or 2; and
u is 1 or 2.

12. A compound according to claim 11, or a stereoisomer or a pharmaceutically-acceptable salt thereof, wherein Z is

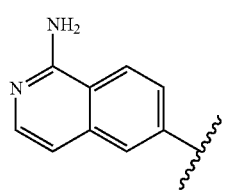

13. A compound according to claim 1, wherein:
X is NR$_5$(benzyl) optionally substituted with one to two $R_{25}$;
W is hydrogen;
Z is

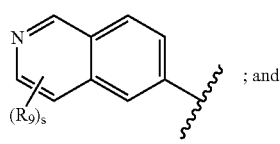

R25 at each occurrence is selected from halogen, cyano, nitro, $C_{1-10}$alkyl, $C_{2-10}$alkenyl, substituted $C_{1-10}$alkyl, substituted $C_{2-10}$alkenyl, —C(=O)NR$_{12}$R$_{13}$, —OR$_{12}$, —CO$_2$R$_{12}$, —C(=O)R$_{12}$, —SR$_{12}$, —S(O)$_r$R$_{15}$, —NR$_{12}$R$_{13}$, —NR$_{12}$SO$_2$R$_{15}$, —NR$_{14}$SO$_2$NR$_{12}$R$_{13}$, —NR$_{12}$CO$_2$R$_{13}$, —NR$_{12}$C(=O)R$_{13}$, —NR$_{14}$C(=O)NR$_{12}$R$_{13}$, —SO$_2$NR$_{12}$R$_{13}$, aryl, heteroaryl, cycloalkyl, and heterocyclo.

14. A compound according to claim 13, wherein:
Z is

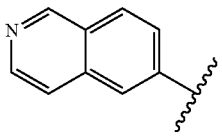

15. A compound according to claim 13, wherein:
Z is

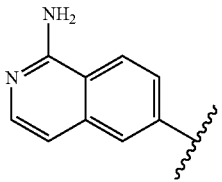

16. A compound according to claim 1, wherein:
X is OH;
W is hydrogen; and
Z is

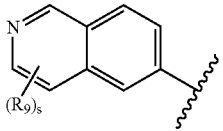

17. A compound according to claim 16, wherein:
Z is

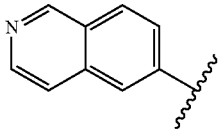

18. A compound according to claim 16, wherein:
Z is

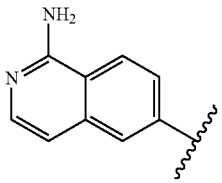

19. A compound according to claim 1, wherein the compound is selected from the group:
(1-Amino-isoquinolin-6-ylamino)-(3-ethoxy-4-isopropoxy-phenyl)-acetic acid; and
2-(1-Amino-isoquinolin-6-ylamino)-N-benzyl-2-(3-ethoxy-4-isopropoxy-phenyl)-acetamide; or a stereoisomer or a pharmaceutically-acceptable salt thereof.

20. A pharmaceutical composition, comprising: a pharmaceutically acceptable carrier and a therapeutically effective amount of a compound of claim 1, or a stereoisomer or a pharmaceutically-acceptable salt thereof.

21. A method for treating a thrombosis, comprising: administering to a patient in need thereof a therapeutically effective amount of a compound of claim 1, or a stereoisomer or a pharmaceutically acceptable salt thereof.

22. A method according to claim 21, wherein the thrombosis is selected from the group consisting of arterial thrombosis, venous thrombosis, deep vein thrombosis and cerebral thrombosis.

23. A pharmaceutical composition, comprising: a pharmaceutically acceptable carrier and a therapeutically effective amount of a compound of claim 2, or a stereoisomer or a pharmaceutically-acceptable salt thereof.

24. A pharmaceutical composition, comprising: a pharmaceutically acceptable carrier and a therapeutically effective amount of a compound of claim 3, or a stereoisomer or a pharmaceutically-acceptable salt thereof.

25. A pharmaceutical composition, comprising: a pharmaceutically acceptable carrier and a therapeutically effective amount of a compound of claim 4, or a stereoisomer or a pharmaceutically-acceptable salt thereof.

26. A pharmaceutical composition, comprising: a pharmaceutically acceptable carrier and a therapeutically effective amount of a compound of claim 5, or a stereoisomer or a pharmaceutically-acceptable salt thereof.

27. A pharmaceutical composition, comprising: a pharmaceutically acceptable carrier and a therapeutically effective amount of a compound of claim 6, or a stereoisomer or a pharmaceutically-acceptable salt thereof.

28. A pharmaceutical composition, comprising: a pharmaceutically acceptable carrier and a therapeutically effective amount of a compound of claim 7, or a stereoisomer or a pharmaceutically-acceptable salt thereof.

29. A pharmaceutical composition, comprising: a pharmaceutically acceptable carrier and a therapeutically effective amount of a compound of claim 8, or a stereoisomer or a pharmaceutically-acceptable salt thereof.

30. A pharmaceutical composition, comprising: a pharmaceutically acceptable carrier and a therapeutically effective amount of a compound of claim 9, or a stereoisomer or a pharmaceutically-acceptable salt thereof.

31. A pharmaceutical composition, comprising: a pharmaceutically acceptable carrier and a therapeutically effective amount of a compound of claim 10, or a stereoisomer or a pharmaceutically-acceptable salt thereof.

32. A pharmaceutical composition, comprising: a pharmaceutically acceptable carrier and a therapeutically effective amount of a compound of claim 11, or a stereoisomer or a pharmaceutically-acceptable salt thereof.

33. A pharmaceutical composition, comprising: a pharmaceutically acceptable carrier and a therapeutically effective amount of a compound of claim 12, or a stereoisomer or a pharmaceutically-acceptable salt thereof.

34. A pharmaceutical composition, comprising: a pharmaceutically acceptable carrier and a therapeutically effective amount of a compound of claim 13, or a stereoisomer or a pharmaceutically-acceptable salt thereof.

35. A pharmaceutical composition, comprising: a pharmaceutically acceptable carrier and a therapeutically effective amount of a compound of claim 14, or a stereoisomer or a pharmaceutically-acceptable salt thereof.

36. A pharmaceutical composition, comprising: a pharmaceutically acceptable carrier and a therapeutically effective amount of a compound of claim 15, or a stereoisomer or a pharmaceutically-acceptable salt thereof.

37. A pharmaceutical composition, comprising: a pharmaceutically acceptable carrier and a therapeutically effective amount of a compound of claim 16, or a stereoisomer or a pharmaceutically-acceptable salt thereof.

38. A pharmaceutical composition, comprising: a pharmaceutically acceptable carrier and a therapeutically effective amount of a compound of claim 17, or a stereoisomer or a pharmaceutically-acceptable salt thereof.

39. A pharmaceutical composition, comprising: a pharmaceutically acceptable carrier and a therapeutically effective amount of a compound of claim 18, or a stereoisomer or a pharmaceutically-acceptable salt thereof.

40. A pharmaceutical composition, comprising: a pharmaceutically acceptable carrier and a therapeutically effective amount of a compound of claim 19, or a stereoisomer or a pharmaceutically-acceptable salt thereof.

\* \* \* \* \*